(12) United States Patent
Pigazzi

(10) Patent No.: US 10,413,643 B2
(45) Date of Patent: Sep. 17, 2019

(54) DEVICES AND METHODS FOR CLEANING CONTAMINATED BODY CAVITIES

(71) Applicant: Alessio Pigazzi, Santa Monica, CA (US)

(72) Inventor: Alessio Pigazzi, Santa Monica, CA (US)

(*) Notice: Subject to any disclaimer, the term of this patent is extended or adjusted under 35 U.S.C. 154(b) by 554 days.

(21) Appl. No.: 14/959,908

(22) Filed: Dec. 4, 2015

(65) Prior Publication Data

US 2016/0158423 A1 Jun. 9, 2016

Related U.S. Application Data

(60) Provisional application No. 62/087,398, filed on Dec. 4, 2014.

(51) Int. Cl.
*A61M 1/00* (2006.01)
*A61M 3/02* (2006.01)
*A61B 17/22* (2006.01)

(52) U.S. Cl.
CPC ........ *A61M 1/0058* (2013.01); *A61M 1/0084* (2013.01); *A61M 3/0283* (2013.01); *A61B 2017/22037* (2013.01); *A61M 2210/106* (2013.01); *A61M 2210/1064* (2013.01)

(58) Field of Classification Search
CPC .............. A61M 1/0058; A61M 1/0084; A61M 3/0283; A61M 2210/106; A61M 2210/1064; A61B 2017/22037
See application file for complete search history.

(56) References Cited

U.S. PATENT DOCUMENTS

| | | | |
|---|---|---|---|
| 693,358 A * | 2/1902 | Westlake | A61M 3/0283 604/39 |
| 5,322,070 A | 6/1994 | Goodman et al. | |
| 5,578,017 A | 11/1996 | Aguilar et al. | |
| 6,544,237 B1 | 4/2003 | Phan | |
| 6,671,892 B1 | 1/2004 | Plyant | |
| 6,692,473 B2 | 2/2004 | St. Cyr et al. | |
| 7,913,329 B2 | 3/2011 | Smith | |
| 8,079,988 B2 | 12/2011 | Beechie | |
| 8,105,335 B1 | 1/2012 | Bentley | |
| 8,607,800 B2 | 12/2013 | Thapliyal et al. | |
| 2005/0256464 A1 * | 11/2005 | Pallas | A61B 17/320708 604/319 |

* cited by examiner

*Primary Examiner* — Nathan R Price
*Assistant Examiner* — John A Doubrava
(74) *Attorney, Agent, or Firm* — The Webb Law Firm

(57) ABSTRACT

An apparatus includes a housing, a first cannula, and a second cannula. The housing defines an inner volume having a first portion in fluid communication with a first set of openings, and a second portion in fluid communication with a second set of openings and fluidically isolated from the first portion. The first cannula has a proximal end portion fluidically couplable to a vacuum source and a distal end portion coupled to the housing such that the first portion of the inner volume and a lumen defined by the first cannula fluidically couple the first openings to the vacuum source. The second cannula has a proximal end portion fluidically couplable to a fluid source and a distal end portion coupled to the housing such that the second portion of the inner volume and a lumen defined by the second cannula fluidically couple the second openings to the fluid source.

7 Claims, 9 Drawing Sheets

DEVICES AND METHODS FOR CLEANING CONTAMINATED BODY CAVITIES

CROSS-REFERENCE TO RELATED APPLICATIONS

This application claims priority to U.S. Provisional Application No. 62/087,398, entitled "Devices and Methods for Cleaning Contaminated Body Cavities," filed Dec. 4, 2014, the disclosure of which is incorporated herein by reference in its entirety.

BACKGROUND

The embodiments described herein relate generally to cleaning contaminated body cavities, and more particularly, to devices and methods for the cleansing of portions of the lower gastrointestinal (GI) tract.

Today, many anatomical structures once considered beyond the realm of diagnostic evaluation and therapeutic intervention can be visualized and treated such as structures of the lower GI tract. By way of example, endoscopic procedures can be used in diagnostic evaluation and therapeutic intervention of the rectum, colon, small intestine, duodenum, and stomach. Generally, in diagnostic and treatment procedures of many GI disorders such as, for example, foreign body removal, gallstone removal, polyp removal, tissue biopsy, structure dilatation, stent placement (for patency and drainage), alleviation of constipation and/or fecal impaction, and haemostasis, among others, it is desirable to visually inspect, access, and/or cleanse portions of the GI tract.

In some instances, during routine diagnostic colonoscopies and/or during more complicated treatments of acute lower GI dysfunction, it is common to encounter mucus secretions, stool, and or bleeding which limits the visualization and/or therapeutic capabilities. While common, such mucus secretions, stool, and/or bleeds can introduce contaminants into portions of the lower GI tract, which can lead to increased risks of infection, morbidity, or mortality associated with surgical intervention or the like. Thus, to aid in visualization and/or cleaning of the lower GI tract, sterile water, saline, or other solutions are often used as irrigation or lavage. While devices are known to provide such functionality, some such devices are cumbersome, inefficient, and/or overly uncomfortable for patients. Moreover, in some instances, a device configured to provide irrigation, while used in conjunction, is independent of a device configured to provide suction or the like (i.e., non-integral, non-integrated, and/or otherwise not sharing a common structure).

Thus, a need exists for improved devices and methods for cleaning contaminated body cavities such as, for example, the lower gastrointestinal tract or other body cavities.

SUMMARY

Devices and methods for cleaning contaminated body cavities such as portions of the lower GI tract are described herein. In some embodiments, an apparatus includes a housing having a proximal end portion and a distal end portion, and defining an inner volume; a first cannula having a proximal end portion and a distal end portion, and defining a lumen therethrough; and a second cannula having a proximal end portion and a distal end portion, and defining a lumen therethrough. The proximal end portion of the housing defines a first set of openings in fluid communication with a first portion of the inner volume. The distal end portion of the housing defines a second set of openings in fluid communication with a second portion of the inner volume, fluidically isolated from the first portion. The proximal end portion of the first cannula is configured to be fluidically coupled to a vacuum source. The distal end portion of the first cannula is disposed in the inner volume to place the lumen of the first cannula in fluid communication with the first portion of the inner volume such that the first portion of the inner volume and the lumen of the first cannula collectively define a fluid flow path between the first set of openings and the vacuum source. The proximal end portion of the second cannula is configured to be fluidically coupled to a fluid source. The distal end portion of the second cannula is disposed in the inner volume to place the lumen of the second cannula in fluid communication with the second portion of the inner volume. The second portion of the inner volume and the lumen of the second cannula collectively define a fluid flow path between the second set of openings and the fluid source.

DETAILED DESCRIPTION

Figure 1:
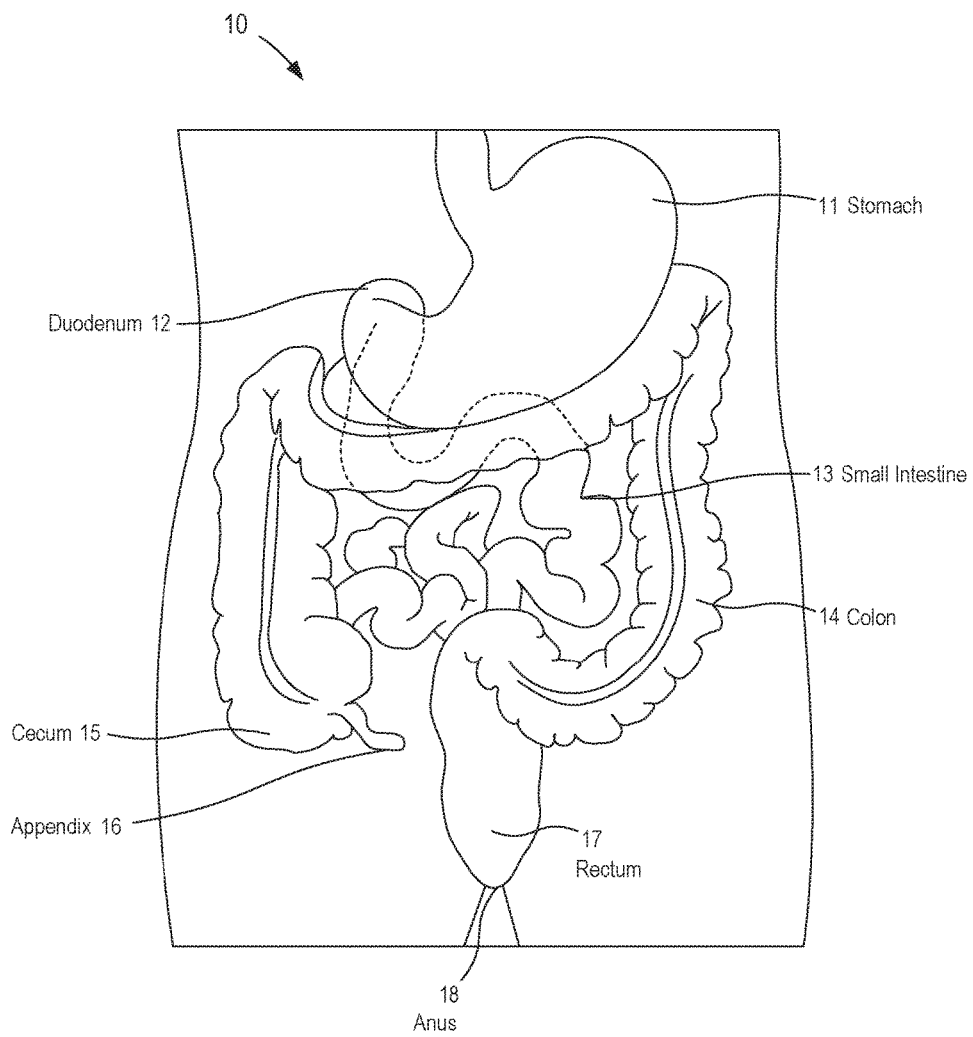
FIG. 1 is a schematic illustration of a portion of the human body showing at least a portion of the anatomic structures of the lower GI tract.

In some embodiments, an apparatus includes a housing, a first cannula, and a second cannula. The housing has a proximal end portion and a distal end portion and defines an inner volume. The housing defines a first plurality of openings in fluid communication with a first portion of the inner volume and a second plurality of openings in fluid communication with a second portion of the inner volume. The first portion of the inner volume is fluidically isolated from the second portion of the inner volume. The first cannula has a proximal end portion and a distal end portion and defines a lumen therethrough. The proximal end portion of the first cannula is configured to be placed in fluid communication with a vacuum source. The distal end portion of the first cannula is coupled to the housing such that the first portion of the inner volume and the lumen of the first cannula collectively define a fluid flow path between the first plurality of openings and the vacuum source. The second cannula has a proximal end portion and a distal end portion and defines a lumen therethrough. The proximal end portion of the second cannula is configured to be placed in fluid communication with a fluid source. The distal end portion of the second cannula is coupled to the housing such that the second portion of the inner volume and the lumen of the second cannula collectively define a fluid flow path between the second plurality of openings and the fluid source.

In some embodiments, an apparatus includes a housing, a first conduit, a second conduit, a first cannula, and a second cannula. The housing has a proximal end portion and a distal end portion and defines an inner volume. The distal end portion includes a first port and a second port. The housing defines a first plurality of openings in fluid communication with a first portion of the inner volume and a second plurality of openings in fluid communication with a second portion of the inner volume. The first portion of the inner volume is fluidically isolated from the second portion of the inner volume. The first conduit is disposed in the inner volume, has a proximal end portion and a distal end portion, and defines a lumen therethrough. The distal end portion of the first conduit defines a plurality of openings that places the lumen of the first conduit in fluid communication with the first portion of the inner volume. The lumen of the first conduit is further in fluid communication with a lumen defined by the first port. The second conduit has a proximal end portion and a distal end portion and defines a lumen therethrough. The second conduit is at least partially disposed within the lumen of the first conduit. The lumen of the second conduit, fluidically isolated from the lumen of the first conduit, defines a fluid flow path between the second portion of the inner volume and a lumen defined by the second port. The first cannula has a proximal end portion and a distal end portion and defining a lumen therethrough. The proximal end portion of the first cannula is configured to be placed in fluid communication with a vacuum source. The distal end portion of the first cannula is configured to be coupled to the first port to place the lumen of the first cannula in fluid communication with the lumen of the first conduit. The second cannula has a proximal end portion and a distal end portion and defines a lumen therethrough. The proximal end portion of the second cannula is configured to be placed in fluid communication with a fluid source. The distal end portion of the second cannula is configured to be coupled to the second port to place the lumen of the second cannula in fluid communication with the lumen of the second conduit.

In some embodiments, a method of cleansing a body cavity, using a device having a housing that defines a first plurality of openings in fluid communication with a first portion of an inner volume defined by the housing and a second plurality of openings in fluid communication with a second portion of the inner volume fluidically isolated from the first portion of the inner volume, includes coupling a distal end portion of a first cannula to the housing such that a lumen defined by the first cannula is in fluid communication with the first portion of the inner volume. A proximal end portion of the first cannula is operatively coupled to a vacuum source. A distal end portion of a second cannula is coupled to the housing such that a lumen defined by the second cannula is in fluid communication with the second portion of the inner volume. A proximal end portion of the second cannula is operatively coupled to a fluid source. A portion of the housing is inserted into a body cavity such that each of the first plurality of openings and the second plurality of openings is disposed within the body cavity. A fluid is conveyed from the fluid source to the body cavity via the lumen defined by the second cannula, the second portion of the inner volume, and the second plurality of openings. A fluid is withdrawn from the body cavity into the vacuum source, substantially concurrently with the conveying the fluid, via the lumen defined by the first cannula, the first portion of the inner volume, and the first plurality of openings.

In some embodiments, an apparatus includes a housing having a proximal end portion and a distal end portion, and defining an inner volume; a first cannula having a proximal end portion and a distal end portion, and defining a lumen therethrough; and a second cannula having a proximal end portion and a distal end portion, and defining a lumen therethrough. The proximal end portion of the housing defines a first set of openings in fluid communication with a first portion of the inner volume. The distal end portion of the housing defines a second set of openings in fluid communication with a second portion of the inner volume, fluidically isolated from the first portion. The proximal end portion of the first cannula is configured to be fluidically coupled to a vacuum source. The distal end portion of the first cannula is disposed in the inner volume to place the lumen of the first cannula in fluid communication with the first portion of the inner volume such that the first portion of the inner volume and the lumen of the first cannula collectively define a fluid flow path between the first set of openings and the vacuum source. The proximal end portion of the second cannula is configured to be fluidically coupled to a fluid source. The distal end portion of the second cannula is disposed in the inner volume to place the lumen of the second cannula in fluid communication with the second portion of the inner volume. The second portion of the inner volume and the lumen of the second cannula collectively define a fluid flow path between the second set of openings and the fluid source.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method). By way of another example, when referring to a set of opening, the set of openings can include multiple openings or a single opening.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user of the medical device, would be the proximal end of the medical device. Said another way, the distal end portion is the end that is located furthest from a point of reference, such as an origin or a point of attachment. For example, the distal end portion would be the end farthest away from a user's hand. The proximal end portion, thus, would be the position nearer to a point of reference such as an origin, i.e., the user's hand.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

The embodiments and methods described herein can be used, for example, to facilitate visualization, cleaning, and/or treatment of various target tissues, such as, for example, tissue of an anatomic structure of the lower gastrointestinal tract. For reference, FIG. 1 is a cross-sectional view of a portion of the human GI tract 10 and specifically, the lower GI tract. While specific regions and/or structures are identified, it is to be understood that the proceeding identified regions and/or structures do not solely constitute the lower GI tract 10, rather the identified regions are presented as a simplified example suitable for the discussion of the embodiments herein.

As shown in FIG. 1, the lower GI tract 10 of a human receives partially digested food from the intestine and the stomach 11 and functions to absorb remaining nutrients included therein. The lower GI tract 10 includes part of the small intestine 13 and all of the large intestine 14 (also referred to as the colon). Specifically, the duodenum 12 receives partially digested food from the stomach 11, as well as digestive enzymes from the stomach 11, pancreas (not shown in FIG. 1), and the gallbladder (not shown in FIG. 1). The small intestine 13 begins at the duodenum 12 and ends at the cecum of the colon 14. The colon 14 includes the cecum 15 and the appendix 16 at a first end (e.g., an upstream end), and the rectum 17 and anus 18 at a second end (e.g., a downstream end). Thus, as food passes through the lower GI tract 10, the small intestine 13 generally absorbs nutrients and/or other useful products of digestion (e.g., carbohydrates, proteins, lipids, etc.), and the large intestine 14 generally absorbs water resulting in fecal matter that is excreted by through the anus 18.

Figure 2:
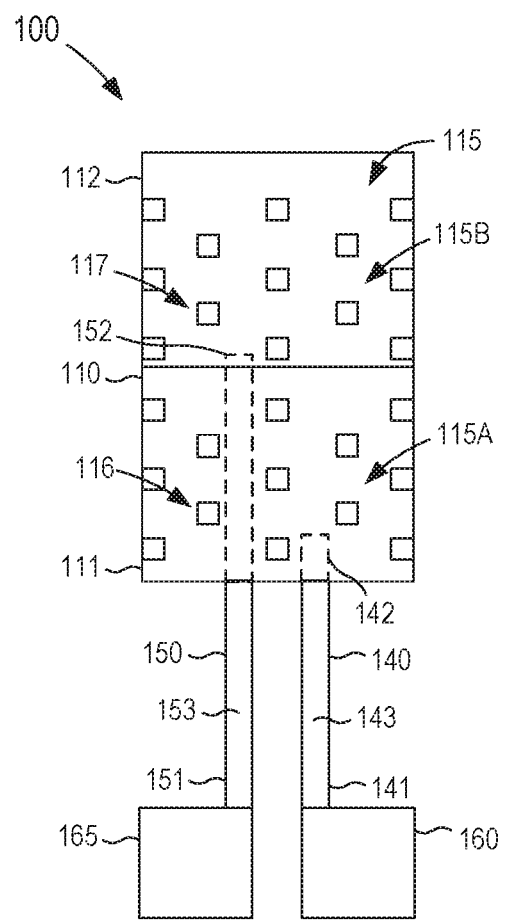
FIG. 2 is a schematic illustration of a body cavity cleansing device according to an embodiment.

Referring now to FIG. 2, a body cavity cleansing device 100 is illustrated according to an embodiment. The body cavity cleansing device 100 (also referred to herein as "device") includes a housing 110, a first cannula 140, and a second cannula 150. In some instances, the device 100 is used to facilitate the cleaning of a body cavity such as, for example, a portion of the lower GI tract 10 illustrated in FIG. 1. Specifically, a portion of the housing 110 can be inserted through the anus 18 to gain access to a cavity (e.g., a lumen or the like) defined by the rectum 17 and/or the colon 14. Thus, with a healthy lower GI tract 10 defining a continuous, albeit tortuous, lumen between the stomach 11 and the anus 18, inserting a portion of the housing 110 into the anus 18 places the housing 110 in fluid communication with the substantially all of the lower GI tract 10, as described in further detail herein.

As shown in FIG. 2, the housing 110 includes a proximal end portion 111 and a distal end portion 112 and defines an inner volume 115. The housing 110 can be any suitable shape, size, or configuration. For example, in some embodiments, the housing 110 is formed by and/or otherwise includes a set of annular walls extending from the proximal end portion 111 to the distal end portion 112. Similarly, the housing 110 can be formed from and/or can include any suitable material such as, for example, any of those described above. In some embodiments, the arrangement of the housing 110 substantially corresponds to an anatomical structure of the lower GI tract 10. By way of example, the size, shape, and stiffness of the housing 110 can be suitable for insertion into the body (i.e., via the anus 18), while limiting discomfort and/or substantially preventing injury of the patient. Moreover, the proximal end portion 111 is substantially open to receive a portion of the first cannula 140 and a portion of the second cannula 150, and the distal end portion 112 is closed having a distal end surface that can be, for example, substantially rounded or the like.

The housing 110 defines a first set of openings 116 and a second set of openings 117. More specifically, in some embodiments, the proximal end portion 111 can define the first set of openings 116 arranged along the circumference of the housing 110 (e.g., in the circumferential direction and in the axial direction) and extending through a wall of the housing 110 to be in fluid communication with, for example, a first portion 115A of the inner volume 115. Similarly, the distal end portion 112 can define the second set of openings 117 arranged along the circumference of the housing 110 (e.g., in the circumferential direction and in the axial direction) and extending through a wall of the housing 110 to be in fluid communication with, for example, a second portion 115B of the inner volume 115.

The arrangement of the housing 110 can be such that the first portion 115A of the inner volume 115 is substantially fluidically isolated from the second portion 115B of the inner volume 115. For example, in some embodiments, the housing 110 can define two distinct volume, reservoirs, cavities, void, etc., which are isolated from one another by a wall or the like. In other embodiments, the inner volume 115 is a single continuous volume that is separated into the first portion and the second portion via a seal member or the like configured to form a substantially fluid tight seal with an inner surface of the housing 110, thereby fluidically isolating the first portion from the second portion.

When referring to the substantially fluidic isolation between the first portion 115A of the inner volume 115 and the second portion 115B of the inner volume 115, the fluidic isolation therebetween is described relative to the inner volume 115 defined by the housing 110. Thus, while the first set of openings 116 and the second set of openings 117 place the first portion and the second portion, respectively, of the inner volume 115 in fluid communication with a volume substantially outside of the housing 110, which in turn, may place the first set of openings 116 in fluid communication with the second set of openings 117, the first portion 115A of the inner volume 115 and the second portion 115B of the inner volume 115 are nonetheless substantially fluidically isolated within the context of a volume defined by the housing 110.

As shown in FIG. 2, the first cannula 140 has a proximal end portion 141 and a distal end portion 142 and defines a lumen 143 therethrough. The proximal end portion 141 of the first cannula 140 can be operably coupled to a vacuum source 160 such that the lumen 143 is placed in fluid communication with the vacuum source 160. For example, in some embodiments, the proximal end portion 141 can be physically and fluidically coupled to the vacuum source 160. In other embodiments, the proximal end portion 141 of the first cannula 140 can be coupled to the vacuum source 160 via an intervening structure such as, for example, a locking mechanism, a valve, a coupler, flexible sterile tubing, and/or the like.

As shown in FIG. 2, a portion of the first cannula 140 is disposed within the housing 110 such that the lumen 143 is in fluid communication with the first portion 115A of the inner volume 115 and thus, in fluid communication with the first set of openings 116. For example, in some embodiments, the distal end portion 142 of the first cannula 140 can be disposed within the first portion 115A of the inner volume 115. In other embodiments, the distal end portion 142 of the first cannula 140 can be physically and fluidically coupled to a port or the like included in and/or defined by, for example, a proximal surface of the housing 110. Moreover, with the first cannula 140 being disposed, for example, proximal to a seal member or the like configured to fluidically isolate the first portion 115A of the inner volume 115 from the second portion 115B of the inner volume 115, the lumen 143 of the first cannula 140 is in fluid communication with the first portion 115A of the inner volume 115 while being fluidically isolated from the second portion 115B of the inner volume 115.

In a similar manner, the second cannula 150 has a proximal end portion 151 and a distal end portion 152 and defines a lumen 153 therethrough. The proximal end portion 151 of the second cannula 150 can be operably coupled to a fluid source 165 such that the lumen 153 is placed in fluid communication with the fluid source 165. For example, in some embodiments, the proximal end portion 151 can be physically and fluidically coupled to the fluid source 165. In other embodiments, the proximal end portion 151 of the second cannula 150 can be coupled to the fluid source 165 via an intervening structure such as, for example, a locking mechanism, a valve, a coupler, flexible sterile tubing, and/or the like.

As shown in FIG. 2, a portion of the second cannula 150 is disposed within the housing 110 such that the lumen 153 is in fluid communication with the second portion 115B of the inner volume 115 and thus, in fluid communication with the second set of openings 117. For example, with the first portion 115A of the inner volume 115 substantially fluidically isolated from the second portion 115B of the inner volume 115, the distal end portion 152 of the first cannula can be coupled to a port and/or otherwise at least partially extend through a seal member and/or wall fluidically isolating the first portion 115A of the inner volume 115 from the second portion 115B of the inner volume 115. In some embodiments, the housing 110 can include and/or can define a conduit to which the second cannula 150 can be physically and fluidically coupled to place the lumen 153 in fluid communication with the second portion 115B of the inner volume 115. Moreover, the arrangement of the housing 110 and the second cannula 150 is such that the lumen 153 defined by the second cannula 150 is substantially fluidically isolated from the first portion 115A of the inner volume 115, as described in further detail herein.

In use, a user can manipulate the device 100, for example, by fluidically coupling the first cannula 140 to the vacuum source 160 and the second cannula 150 to the fluid source 165. The vacuum source 160 and the fluid source 165 can be any suitable devices, machines, mechanisms, and/or the like. For example, in some embodiments, the vacuum source 160 can include a pump or the like and a reservoir such as a waste reservoir and/or biohazard receptacle. The fluid source 165 can include a fluid reservoir containing sterile water, saline, or the like and a pump configured to increase a pressure of a volume of the sterile water, saline, or the like. In some embodiments, the vacuum source 160 and the fluid source 165 can be a single device to which both the first cannula 140 and the second cannula 150 are coupled. In other embodiments, the vacuum source 160 and the fluid source 165 can be separate units and/or devices.

Once the first cannula 140 and the second cannula 150 are fluidically coupled (either directly or indirectly) to the vacuum source 160 and the fluid source 165, respectively, the user can then manipulate the device 100 by inserting at least a portion of the housing 110 into, for example, the anus 18 of the body (e.g., his or her body or in the case of a user being a medical professional, a patient's body). As such, the first set of openings 116 and the second set of openings 117 are disposed within a portion of the anal canal, the rectum 17, or the colon 14 of the lower GI tract (see e.g., FIG. 1). With the housing 110 disposed in the desired position within, for example, the lower GI tract 10, the user can actuate the device 100 and/or the vacuum source 160 and the fluid source 165. In this manner, the fluid source 165, once actuated, can produce a pressurized flow of sterile water or saline, which in turn, flows through the lumen 153 of the second cannula 150, into the second portion of the inner volume 115 of the housing 110, and through the second set of openings 117. The vacuum source 160, once actuated, can produce a negative pressure differential between the vacuum source 160 and the lumen 143 of the first cannula 140, which in turn, produces a suction force within the lumen 143. Thus, with the lumen 143 in fluid communication with the first portion 115A of the inner volume 115, a suction force is exerted in and/or through the first portion 115A of the inner volume 115 and through the first set of openings 116.

As such, the device 100 can provide lavage of the lower GI tract 10. More specifically, the pressurized flow of sterile water or saline flows through the second cannula 150 and the second set of openings 117 and into the lumen defined by a portion of the lower GI tract 10, which in turn, can rinse, cleanse, break apart, and/or otherwise solubilize undesired matter (e.g., fecal matter, pus, blood, undigested food particles, bacteria, etc.). In addition, the negative pressure differential produced by the vacuum source 160 can substantially concurrently exert a suction force through the first set of openings 116, which in turn, draws such undesired matter that is broken apart, solubilized, and/or otherwise released by the pressurized flow of sterile water or saline, as well as a waste portion of the used water (i.e., no longer sterile) into the first portion 115A of the inner volume 115, through the lumen 143 of the first cannula 140 and into a waste reservoir or storage fluidically coupled to the vacuum source 160. Thus, the device 100 can be used, for example, to cleanse contaminants from a cavity and/or lumen defined, for example, by the lower GI tract 10.

FIGS. 3-10 illustrate a body cavity cleansing device 200 according to another embodiment. The body cavity cleansing device 200 (also referred to herein as "device") includes a housing 210, a first cannula 240, and a second cannula 250. In some instances, the device 200 is used to facilitate the cleaning of a body cavity such as, for example, a portion of the lower GI tract 10 illustrated in FIG. 1. Specifically, a portion of the housing 210 can be inserted through the anus 18 to gain access to a cavity (e.g., a lumen or the like) defined by the rectum 17 and/or the colon 14. Thus, with a healthy lower GI tract 10 defining a continuous, albeit tortuous, lumen between the stomach 11 and the anus 18, the insertion of the portion of the housing 210 into the anus 18 places the housing 210 in fluid communication with the substantially all of the lower GI tract 10, as described in further detail herein.

Figure 3:
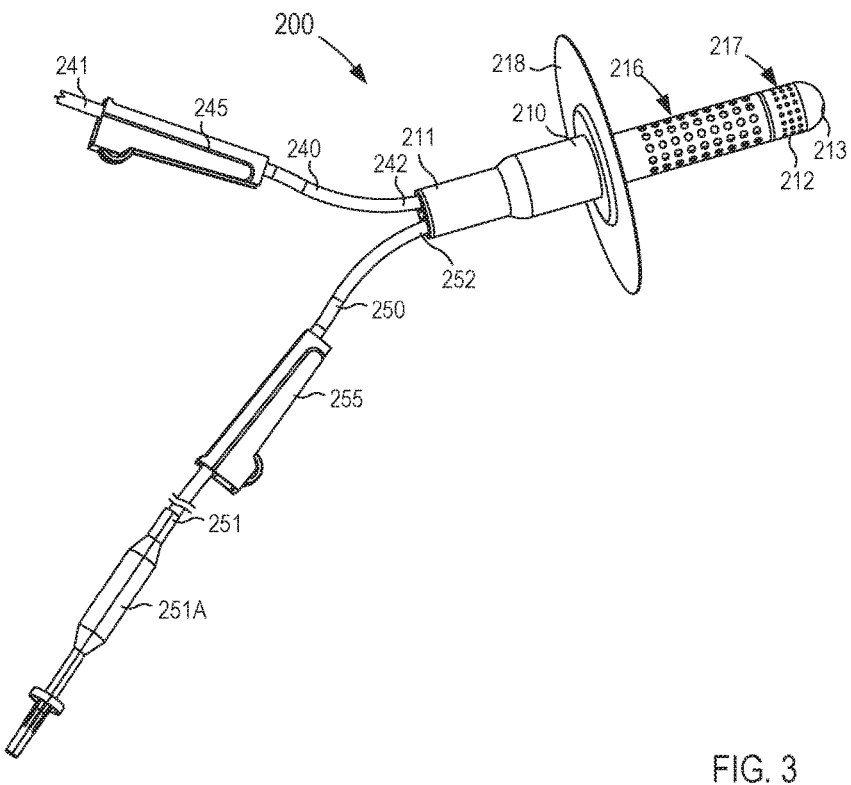
FIGS. 3 and 4 are perspective views of a body cavity cleansing device according to an embodiment.
Figure 4:
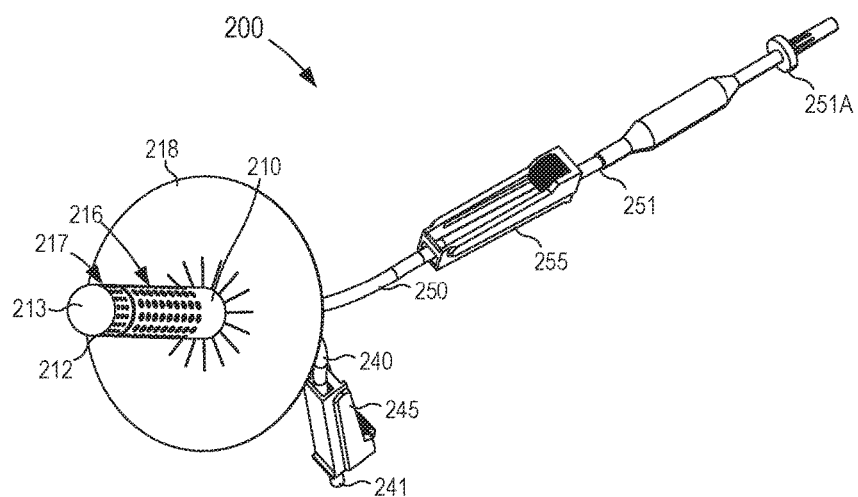
Figure 5:
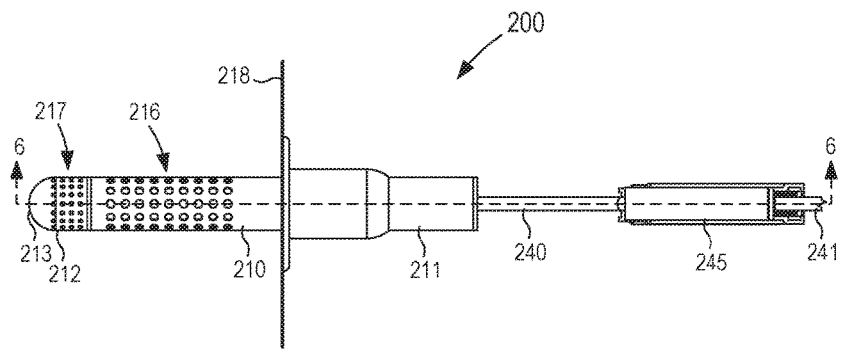
FIG. 5 is a top view of the body cavity cleansing device of FIG. 3.
Figure 6:
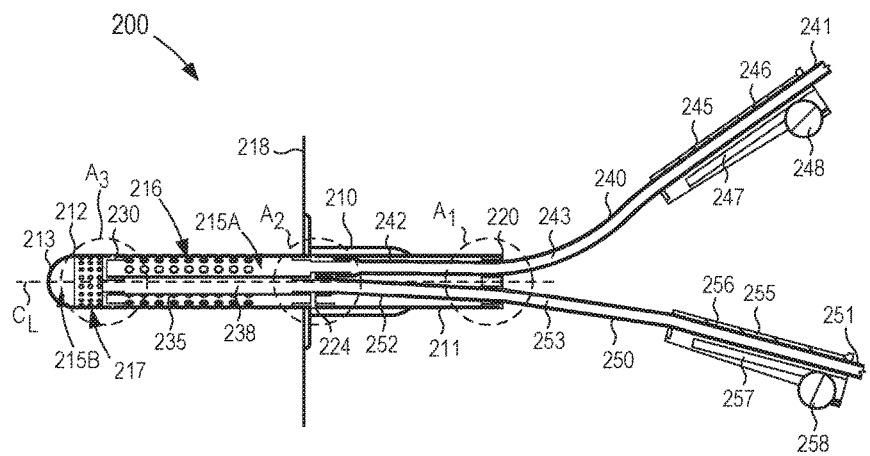
FIG. 6 is a cross-sectional view of the body cavity cleansing device of FIG. 3, taken along the line 6-6 in FIG. 5.

As shown in FIGS. 3-6, the housing 210 includes a proximal end portion 211 and a distal end portion 212 and defines an inner volume 215 (FIG. 6). The housing 210 can be any suitable shape, size, or configuration. For example, in some embodiments, the housing 210 is formed by and/or otherwise includes a set of annular walls extending from the proximal end portion 211 to the distal end portion 212. Said another way, the housing 210 is substantially cylindrical. Similarly, the housing 210 can be formed from and/or can include any suitable material such as, for example, any of the biocompatible materials described above. In some embodiments, the arrangement of the housing 210 substantially corresponds to an anatomical structure of the lower GI tract 10. By way of example, the size, shape, and stiffness of the housing 210 can be suitable for insertion into the body (i.e., via the anus 18), while limiting discomfort and/or substantially preventing injury of the patient. Although shown and described as being substantially cylindrical, in other embodiments, the housing 210 can include and/or can form a slight bend and/or radius that can, for example, facilitate the insertion of the housing 210 into the body. Furthermore, as shown in FIGS. 3 and 4, the housing 210 includes and/or is coupled to a flange 218 (e.g., a guard, shield, barrier, and/or the like). In some embodiments, the flange 218 can be movably disposed about a portion of the housing 210. Thus, as the housing 210 is inserted into the body, the flange 218 can be moved into a desired position along a longitudinal centerline $C_L$ (FIG. 6) of the housing 210. In some embodiments, when the device 200 is in use, the flange 218 can be configured to, for example, limit an amount fluid undesirably flowing outside of the body.

The proximal end portion 211 of the housing 210 is substantially open and is configured to receive a portion of the first cannula 240 and the second cannula 250. Thus, the size and/or shape of the housing 210 and more specifically, the inner volume 215 defined by the housing 210 can be associated with the first cannula 240 and the second cannula 250. That is to say, the housing 210 can be arranged such that a diameter, perimeter, circumference, and/or the like of the inner volume 215 is sufficiently large to allow a portion of the first cannula 240 and a portion of the second cannula 250 to be inserted through the proximal end portion 211. Moreover, the proximal end portion 211 of the housing 210 is coupled to a proximal seal member 220 configured to form a substantially fluid tight seal with the proximal end portion 211 of the housing 210, as described in further detail herein.

The distal end portion 212 of the housing 210 is closed. That is to say, the distal end portion 212 includes a continuous distal surface 213 (e.g., does not define a distal opening) or the like. As shown, for example, in FIGS. 3-6, the distal surface 213 is substantially rounded having any suitable radius of curvature. In some embodiments, the rounded distal surface 213 can, for example, limit and/or otherwise substantially prevent the housing 210 from damaging tissue or the like while being placed into a desired position within the body. Moreover, the arrangement of the housing 210 is such that its walls have a substantially constant thickness and as such, the rounded shape of the distal surface 213 defines a domed portion of the inner volume 215 or the like. In some embodiments, such an arrangement can allow the distal surface 213 to deform in response to an applied force such as, for example, when navigating the housing 210 within a tortuous path within the body, which in turn, can substantially reduce and/or prevent damage to surrounding tissue.

Although the distal surface 213 is particularly shown in FIG. 6 as being hollow (as described above), in other embodiments, the distal end portion 212 can include, for example, a distal tip or the like that is substantially solid. In some such embodiments, the distal tip can be unitarily formed with the housing 210 or independently formed and coupled thereto. For example, in some embodiments, a portion of a distal tip can be inserted into a distal opening or the like to form a friction fit or the like. In other embodiments, a distal tip can be an over-mold or the like. In still other embodiments, a distal tip can be coupled to the housing 210 via an adhesive, a snap fit, a mechanical fastener, and/or the like. Thus, such a distal tip can have, for example, a stiffness, hardness (or durometer), porosity, and/or the like that is different from the remaining portions of the housing 210. By way of example, in some embodiments, a distal tip can have a relatively low stiffness and/or hardness to allow the distal tip to deform, while the remaining portions of the housing 210 can have a stiffness and/or hardness (or durometer) that is sufficient to limit and/or substantially prevent deformation when being navigated within the body. In other embodiments, the distal tip can have a stiffness and/or hardness that are/is greater than the remaining portions of the housing 210, which in turn, can facilitate the exertion of a force on target matter (e.g., fecal matter, food particles, etc.) within a body cavity, thereby aiding in breaking such matter apart.

As shown in FIGS. 5 and 6, the housing 210 defines a first set of openings 216 and a second set of openings 217. For example, in some embodiments, the distal end portion 212 can define the first set of openings 216 arranged along a first portion of the housing 210, wherein each opening extends through a wall of the housing 210 to be in fluid communication with, for example, a first portion 215A of the inner volume 215 (FIG. 6). Similarly, the distal end portion 212 can define the second set of openings 217 arranged along a second portion of the housing 210, wherein each opening extends through the wall of the housing 210 to be in fluid communication with, for example, a second portion 215B of the inner volume 215. More specifically, the first set of openings 216 are included in and/or form a pattern of openings at or near a first, proximal region along the longitudinal centerline $C_L$ of the housing 210, and the second set of openings 217 are included in and/or form a pattern of openings at or near a second, distal region along the longitudinal centerline $C_L$ of the housing 210.

The openings included in the first set of openings 216 can be any suitable shape or size, and can be arranged in any suitable manner. For example, as shown, the openings in the first set of openings 216 are substantially similar and are arranged in an array (i.e., aligned circumferentially into similar rows and axially into similar columns). In other embodiments, the openings in the first set of openings 216 can be arranged in a staggered or offset pattern (i.e., at least a portion of the openings are not aligned). Moreover, the openings in the first set of openings 216 can each have a substantially similar size. For example, in some embodiments, each opening included in the first set of openings 216 can have a diameter of about 4 millimeters (mm). In other embodiments, each opening in the first set of openings 216 can have a diameter less than 4 mm or greater than 4 mm. In still other embodiments, a diameter of the openings in the first set of openings 216 can be varied. In some embodiments, the shape, size, and/or arrangement of the openings in the first set of openings 216 can, for example, limit, control, and/or otherwise define a fluid flow rate therethrough, as described in further detail herein.

In a similar manner, the openings included in the second set of openings 217 can be any suitable shape or size, and can be arranged in any suitable manner. For example, as shown, the openings in the second set of openings 217 are substantially similar and are disposed in a similar arrangement as described with reference to the first set of openings 216. Moreover, in some embodiments, each opening included in the second set of openings 217 can have a diameter of about 2 millimeters (mm). In other embodiments, each opening in the second set of openings 217 can have a diameter less than 2 mm or greater than 2 mm. In still other embodiments, a diameter of the openings in the second set of openings 217 can be varied. In some embodiments, the shape, size, and/or arrangement of the openings in the second set of openings 217 can, for example, limit, control, and/or otherwise define a fluid flow rate therethrough, as described in further detail herein.

The arrangement of the housing 210 is such that the first portion 215A of the inner volume 215 is substantially fluidically isolated from the second portion 215B of the inner volume 215. For example, as shown in FIGS. 6-9, the housing 210 includes and/or otherwise houses a proximal seal member 220, a medial seal member 225, and a distal seal member 230. The proximal seal member 220 can be any suitable seal or elastomeric member configured to contact an inner surface of the housing 210 to define a substantially fluid tight seal therebetween. For example, in some embodiments, at least a portion of the proximal seal member 220 can have an outer diameter that is greater than an inner diameter of the housing 210. Thus, when disposed within the inner volume 215, the proximal seal member 220 forms a friction fit with the inner surface of the housing 210, which is sufficient to form a substantially fluid tight seal therebetween. Moreover, the proximal seal member 220 defines a first opening 221 and a second opening 222 configured to receive a portion of the first cannula 240 and the second cannula 250, respectively, as described in further detail herein (see e.g., FIG. 7). Although not shown in FIG. 7, in some embodiments, the proximal seal member 220 is configured to be in contact with a portion the first cannula 240 and a portion of the second cannula 250 disposed in the openings 221 and 222, respectively, to form and/or define a fluid tight seal. Thus, the proximal seal member 220 substantially fluidically seals the proximal end portion 211 of the housing 210, as described in further detail herein.

Figure 8:
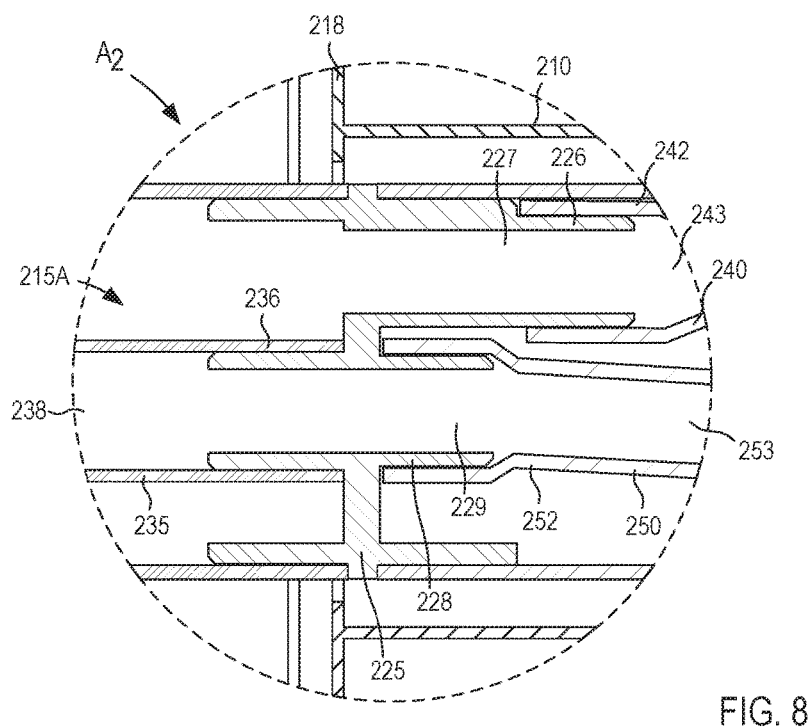

As shown in FIG. 8, the medial seal member 225 is disposed within the inner volume 215 in a medial position along the longitudinal centerline $C_L$. As described above, the medial seal member 225 can be any suitable seal or elastomeric member configured to be in contact with the inner surface of the housing 210 to form and/or define a substantially fluid tight seal therebetween. The medial seal member 225 includes a first coupling portion 226, defining an opening 227, and a second coupling portion 228, defining an opening 229. As shown in FIG. 8, the first coupling portion 226 is coupled to a distal end portion 242 of the first cannula 240 and the second coupling portion 228 is coupled to a distal end portion 252 of the second cannula 250, as described in further detail herein. Moreover, a distal portion of the medial seal member 225 is coupled to, for example, a proximal end portion 236 of a conduit 235 such that a lumen 238 defined by the conduit 235 is in fluid communication with the opening 229 of the second coupling portion 228. As described in further detail herein, the conduit 235 is configured to extend through the first portion 215A of the inner volume 215 to be coupled to the distal seal member 230.

Figure 9:
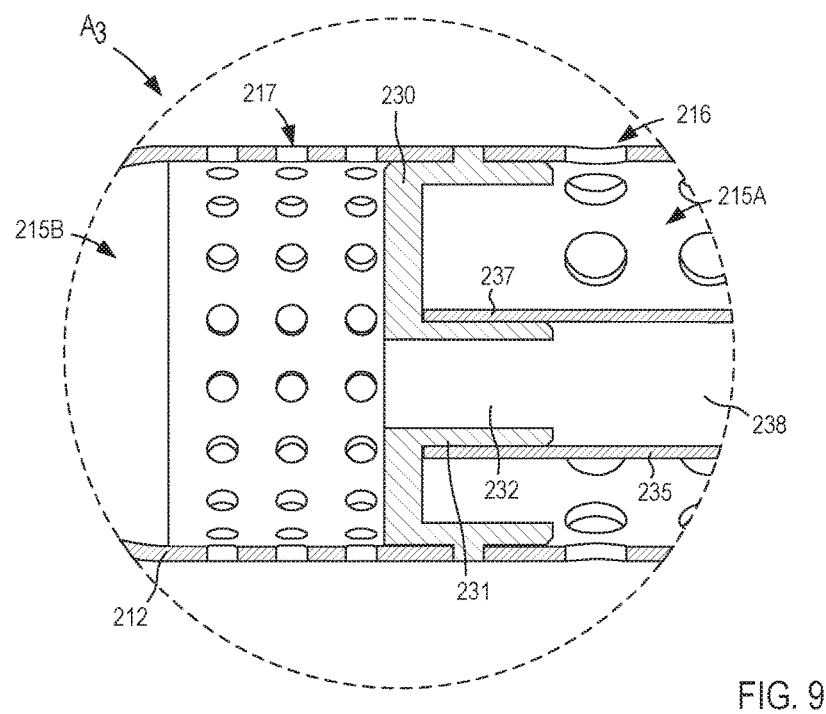

As shown in FIG. 9, the distal seal member 230 is disposed within the inner volume 215 in a distal position along the longitudinal centerline $C_L$. As described above, the distal seal member 230 can be any suitable seal or elastomeric member configured to be in contact with the inner surface of the housing 210 to form and/or define a substantially fluid tight seal therebetween. The distal seal member 230 includes a coupling portion 231 that defines an opening 232. As shown in FIG. 9, the coupling portion 231 of the distal seal member 230 is coupled to a distal end portion 237 of the conduit 235 such that the lumen 238 defined by the conduit 235 is in fluid communication with the opening 232 of the coupling portion 231. Thus, the conduit 235 extends through the first portion 215A of the inner volume 215 to define a fluid flow path in the direction of the longitudinal centerline $C_L$ from a position proximal to the medial seal member 225 to a position distal to the distal seal member 230 (see e.g., FIG. 6).

The arrangement of the medial seal member 225, the distal seal member 230, and the conduit 235, for example, collectively define, separate, and/or isolate the inner volume 215 of the housing 210 into the first portion 215A and the second portion 215B. More specifically, as shown in FIG. 9, the portion of the inner volume 215 that is distal to the distal seal member 230 defines the second portion 215B of the inner volume 215. As shown, for example, in FIGS. 9 and 10, the portion of the inner volume 215 disposed between the distal seal member 230 and the medial seal member 225 defines the first portion 215A of the inner volume 215. That is to say, the portion of the inner volume 215 proximal to the distal seal member 230 and distal to the medial seal member 225 defines the first portion 215A of the inner volume 215. Thus, the arrangement of the medial seal member 225, the distal seal member 230, and the conduit 235 is such that the first portion 215A of the inner volume 215 is substantially fluidically isolated from the second portion 215B of the inner volume 215. Furthermore, the arrangement of the medial seal member 225 and the proximal seal member 220 can, for example, act as a redundancy to inhibit a fluid from flow through the proximal end portion 211 of the housing 210 yet outside of the cannulas 240 and 250.

When referring to the substantially fluidic isolation between the first portion 215A of the inner volume 215 and the second portion 215B of the inner volume 215, the fluidic isolation therebetween is described relative to the inner volume 215 defined by the housing 210. Thus, while the first set of openings 216 and the second set of openings 217 place the first portion and the second portion, respectively, of the inner volume 215 in fluid communication with a volume substantially outside of the housing 210, which in turn, may place the first set of openings 216 and the second set of openings 217 in fluid communication, the first portion 215A of the inner volume 215 and the second portion 215B of the inner volume 215 are nonetheless substantially fluidically isolated within the context of a volume defined by the housing 210.

The first cannula 240 of the device 200 has a proximal end portion 241 and the distal end portion 242 and defines a lumen 243 therethrough. The proximal end portion 241 of the first cannula 240 can be operably coupled to a vacuum source (not shown in FIGS. 3-10) such that the lumen 243 is placed in fluid communication therewith. For example, in some embodiments, the proximal end portion 241 can be physically and fluidically coupled to an inlet of a vacuum source or pump. The pump can be any suitable pump configured to produce a negative pressure differential between a portion of the pump and the inlet of the vacuum source. Thus, when the first cannula 240 is fluidically coupled to the inlet (e.g., either directly or indirectly), activation of the vacuum source results in a suction force within the lumen 243, as described in further detail herein.

As shown in FIGS. 3-6, the proximal end portion 241 is inserted through and/or otherwise partially disposed in, a flow control mechanism 245. The flow control mechanism 245 can be any suitable device, mechanism, member, assembly, and/or the like configured to selectively control a flow of the through the lumen 243 defined by the first cannula 240. Specifically, as shown in FIG. 6, the flow control mechanism 245 defines a channel 246 and control track 247. A portion of the first cannula 240 is disposed within the channel 246. In some embodiments, the channel 246 can have a diameter that is associated with an outer diameter of the first cannula 240 such that when the first cannula 240 is disposed in the channel 246, a surface of the flow control mechanism 245 forms a friction fit with the first cannula 240. In this manner, the flow control mechanism 245 can be maintained in a substantially fixed position about the first cannula 240.

The flow control mechanism 245 includes a control member 248 movably disposed in the track 247 and configured to selectively engage the first cannula 240. For example, the arrangement of the flow control mechanism 245 is such that when the control member 248 is disposed in a proximal position within the track 247, the control member 248 is spaced apart from a surface of the first cannula 240 (FIG. 6). The control member 248 can be moved in the distal direction from the proximal position to be placed in contact with the outer surface of the first cannula 240, which in turn, can deform a portion of the first cannula 240 to at least partially obstruct the lumen 243. For example, in some embodiments, the track 247 can define a path, along which the control member 248 is moved, that is oriented at an angle relative to the channel 246 such that a proximal end portion of the track 247 is spaced apart from the channel 246 by a distance that is greater than a distance at which a distal end portion of the track 247 is spaced apart from the channel 246. Thus, as the control member 248 is moved in the distal direction within the track 247, the control member 248 is moved closer to the first cannula 240. In some embodiments, the position of the control member 248 relative to the channel 246, when in a distal most position within the track 247, can be such that the control member 248 contacts the first cannula 240 a sufficient amount to substantially obstruct and/or pinch the lumen 243, thereby fluidically isolating the proximal end portion 241 of the first cannula 240 from the distal end portion 242.

Figure 7:
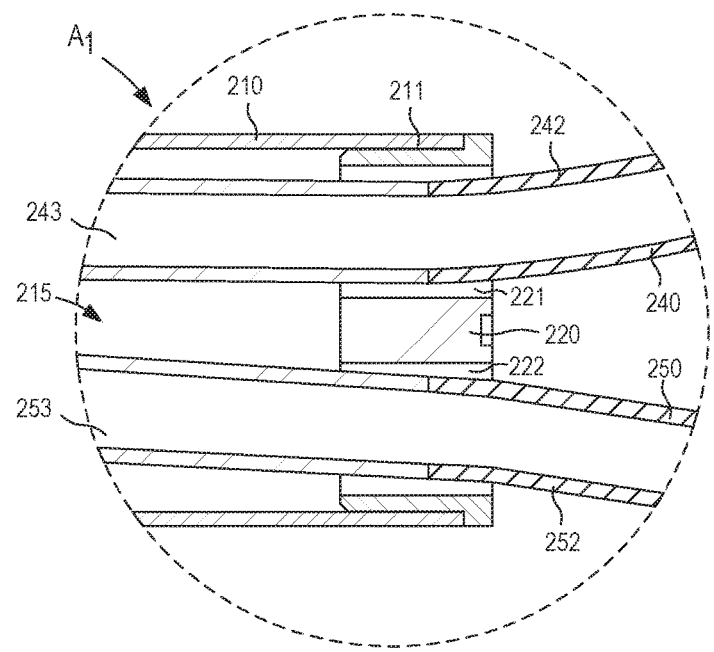
FIGS. 7-9 are enlarged cross-sectional views of a proximal portion, a medial portion, and a distal portion, respectively, of the body cavity cleansing device in FIG. 6, identified by the regions $A_1$, $A_2$, and $A_3$, respectively.

The distal end portion 242 of the first cannula 240 is disposed within the housing 210. More specifically, the distal end portion 242 of the first cannula 240 can be inserted through the first opening 221 of the proximal seal member 220 and coupled to, for example, the first coupling portion 226 of the medial seal member 225, as shown in FIGS. 7 and 8. In this manner, the lumen 243 of the first cannula 240 is in fluid communication with the opening 227 defined by the first coupling portion 226 of the medial seal member 225, which in turn, places the lumen 243 of the first cannula 240 in fluid communication with the first portion 215A of the inner volume 215 (see e.g., FIG. 6). As such, the first portion 215A of the inner volume 215, the opening 227 of the first coupling portion 226 of the medial seal member 225, and the lumen 243 of the first cannula 240 define a fluid flow path between the first set of openings 216 and the vacuum source (not shown), as described in further detail herein.

The second cannula 250 of the device 200 has a proximal end portion 251 and the distal end portion 252 and defines a lumen 253 therethrough. The proximal end portion 251 of the second cannula 250 can be operably coupled to a fluid reservoir (not shown in FIGS. 3-10) such that the lumen 253 is placed in fluid communication therewith. For example, in some embodiments, the proximal end portion 251 can be physically and fluidically coupled to an outlet of a fluid reservoir or the like containing sterile water or saline. In other embodiments, the proximal end portion 251 of the second cannula 250 can be coupled to the fluid source via an intervening structure such as, for example, a locking mechanism, a valve, a coupler, flexible sterile tubing, and/or the like. For example, as shown in FIGS. 3 and 4, the proximal end portion 251 of the second cannula 250 can include a coupling member 251A configured to physically and fluidically couple the second cannula 250 to the fluid source. In some embodiments, the coupling member 251A can be and/or can include a puncture member or the like configured to puncture a septum of the fluid source. In some embodiments, the coupling member can include a filter or the like configured to ensure the sterility of a fluid delivered through the lumen 253 of the second cannula 250. In other embodiments, the second cannula 250 need not include a coupling member 251A. Moreover, although not shown in FIGS. 3-10, in some embodiments, the first cannula 240 can include a coupling member substantially similar to the coupling member 251A.

As shown in FIGS. 3-6, the proximal end portion 251 is inserted through and/or otherwise partially disposed in, a flow control mechanism 255. The flow control mechanism 255 can be any suitable device, mechanism, member, assembly, and/or the like configured to selectively control a flow of the through the lumen 253 defined by the second cannula 250. Specifically, as shown in FIG. 6, the flow control mechanism 255 includes a control member 258 and defines a channel 256 and control track 257. A portion of the second cannula 250 is disposed within the channel 256, as described above with reference to the flow control mechanism 255. The control member 258 is movably disposed in the track 257 and configured to selectively engage the second cannula 250 to obstruct the lumen 253. In this manner, the flow control mechanism 255 can be substantially similar to and/or the same as the flow control member 245 and thus, is not described in further detail herein.

The distal end portion 252 of the second cannula 250 is disposed within the housing 210. More specifically, the distal end portion 252 of the second cannula 250 can be inserted through the second opening 222 of the proximal seal member 220 and coupled to, for example, the second coupling portion 228 of the medial seal member 225, as shown in FIG. 8. In this manner, the lumen 253 of the second cannula 250 is in fluid communication with the opening 229 defined by the second coupling portion 228 of the medial seal member 225, which in turn, places the lumen 253 of the second cannula 250 in fluid communication with the lumen 238 of the conduit 235 (described above). Therefore, with the conduit 235 extending through the first portion 215A of the inner volume 215 to couple to the coupling portion 231 of the distal seal member 230, the lumen 238 of the conduit 235 places the lumen 253 of the second cannula 250 in fluid communication with the second portion 215B of the inner volume 215, as shown in FIG. 9. Moreover, this arrangement places the second cannula 250 in fluid communication with the second portion 215B of the inner volume 215 while maintaining the second cannula 250 in fluidic isolation from the first portion 215A of the inner volume 215. Thus, the second portion 215B of the inner volume 215, the opening 232 of the distal seal member 230, the lumen 238 of the conduit 235, the opening 229 of the second coupling portion 228 of the medial seal member 225, and the lumen 253 of the second cannula 250 define a fluid flow path between the second set of openings 217 and the fluid source (not shown), as described in further detail herein.

Figure 10:
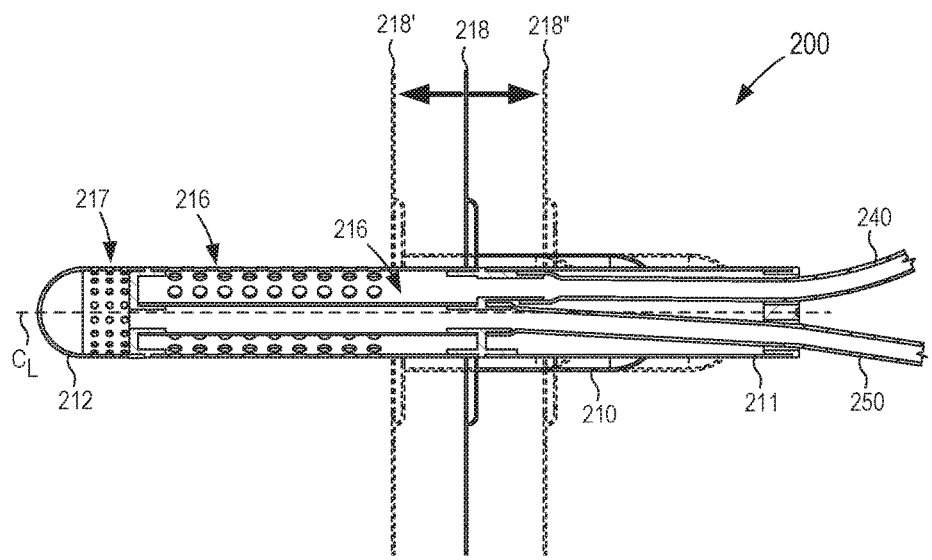
FIG. 10 is a cross-sectional view of a portion of the body cavity cleansing device of FIG. 3, taken along the line 6-6 in FIG. 5.

In use, a user can manipulate the device 200, for example, by fluidically coupling the first cannula 240 to the vacuum source and the second cannula 250 to the fluid source. The user can then manipulate the device 200 by inserting at least a portion of the housing 210 into, for example, the anus 18 of the body (e.g., his or her body or in the case of a user being a medical professional, a patient's body) such that the first set of openings 216 and the second set of openings 217 are disposed within a portion of the anal canal, the rectum 217, or the colon 14 of the lower GI tract (see e.g., FIG. 1). In some instances, the housing 210 can be inserted in to the patient's body at a desired depth that can, for example, place the flange 218 in contact with the skin of the patient. Moreover, as shown in FIG. 10, the flange 218 can be configured to move along the housing 210, for example, to a distal position (e.g., represented by the flange 218') or a proximal position 218". In some instances, the housing 210 can be inserted into the patient's body and the flange 218 can be moved into place thereafter. In other instances, the flange 218 can be placed in a predefined position (e.g., represented by the flange 218' or 218") prior to the insertion of the housing 210 and as such, at least partially controls and/or defines a depth to which the housing 210 is inserted. For example, in some embodiments, the flange 218 can be disposed about the housing 210 and in contact with an outer surface thereof to define a friction fit or the like. In this manner, the position of the flange 218 along, for example, the longitudinal centerline $C_L$ of the housing 210 can be substantially fixed until a force is exerted on the flange 218 that is sufficient to overcome the friction force. In other embodiments, the flange 218 and the housing 210 can form a threaded coupling or the like, whereby rotation of the flange 218 about the housing 210 advances the flange 218 along the longitudinal centerline $C_L$.

With the housing 210 disposed in the desired position within, for example, the lower GI tract 10, the user can actuate the device 200 and/or the vacuum source and the fluid source (not shown in FIGS. 3-10). Specifically, the fluid source, once actuated, can produce a pressurized flow of sterile water or saline ("fluid"), which in turn, flows through the lumen 253 of the second cannula 250, the opening 229 of the second coupling portion 228 of the medial seal member 225, the lumen 238 of the conduit 235 and into the second portion 215B of the of the inner volume 215. In some instances, the flow rate of the fluid (e.g., as produced by a pump or the like included in the fluid source) is such that, a volume of the fluid fills the second portion 215B of the inner volume 215 and thus, once the second portion 215B of the inner volume 215 is substantially filled, an additional flow of fluid increases the pressure within the second portion 215B of the inner volume 215 and thus, forces a pressurized flow of the fluid through the second set of openings 217 and into the body cavity.

In a substantially concurrent process, the vacuum source can be actuated to produce a negative pressure differential between the vacuum source and the lumen 243 of the first cannula 240 (as described above). In this manner, the negative pressure differential produces a suction force within the lumen 243 of the first cannula 240. Thus, with the lumen 243 in fluid communication with the opening 227 defined by the first coupling portion 226 of the medial seal member 225, the suction force within the lumen 243 of the first cannula 240 similarly produces a negative pressure differential between the lumen 243 of the first cannula 240 and the first portion 215A of the inner volume 215. This negative pressure differential produces a corresponding suction force within the first portion 215A of the inner volume 215, and therefore, through the first set of openings 216.

As such, the device 200 can provide lavage of the lower GI tract 10. More specifically, the pressurized flow of sterile water or saline flows through the second cannula 250 and the second set of openings 217 and into the lumen or cavity defined by a portion of the lower GI tract 10, which in turn, can rinse, cleanse, break apart, and/or otherwise solubilize undesired matter (e.g., fecal matter, pus, blood, undigested food particles, bacteria, etc.). In addition, the distal surface 213 of the housing 210 engage such undesired matter, thereby aiding the pressurized flow of fluid in breaking apart the matter. The suction force exerted through the first set of openings 216 draws such undesired matter that is broken apart, solubilized, and/or otherwise released by the pressurized flow of sterile water or saline, as well as a waste portion of the used fluid (i.e., no longer sterile) into the first portion 215A of the inner volume 215. Thus, the undesired matter is drawn through the first portion 215A of the inner volume 215, through the opening 227 defined by the first coupling portion 226 of the medial seal member 225, through the lumen 243 of the first cannula 240 and into, for example, a waste reservoir or storage fluidically coupled to the vacuum source. In this manner, the device 200 can be used, for example, to cleanse contaminants from a cavity and/or lumen defined, for example, by the lower GI tract 10.

Figure 11:
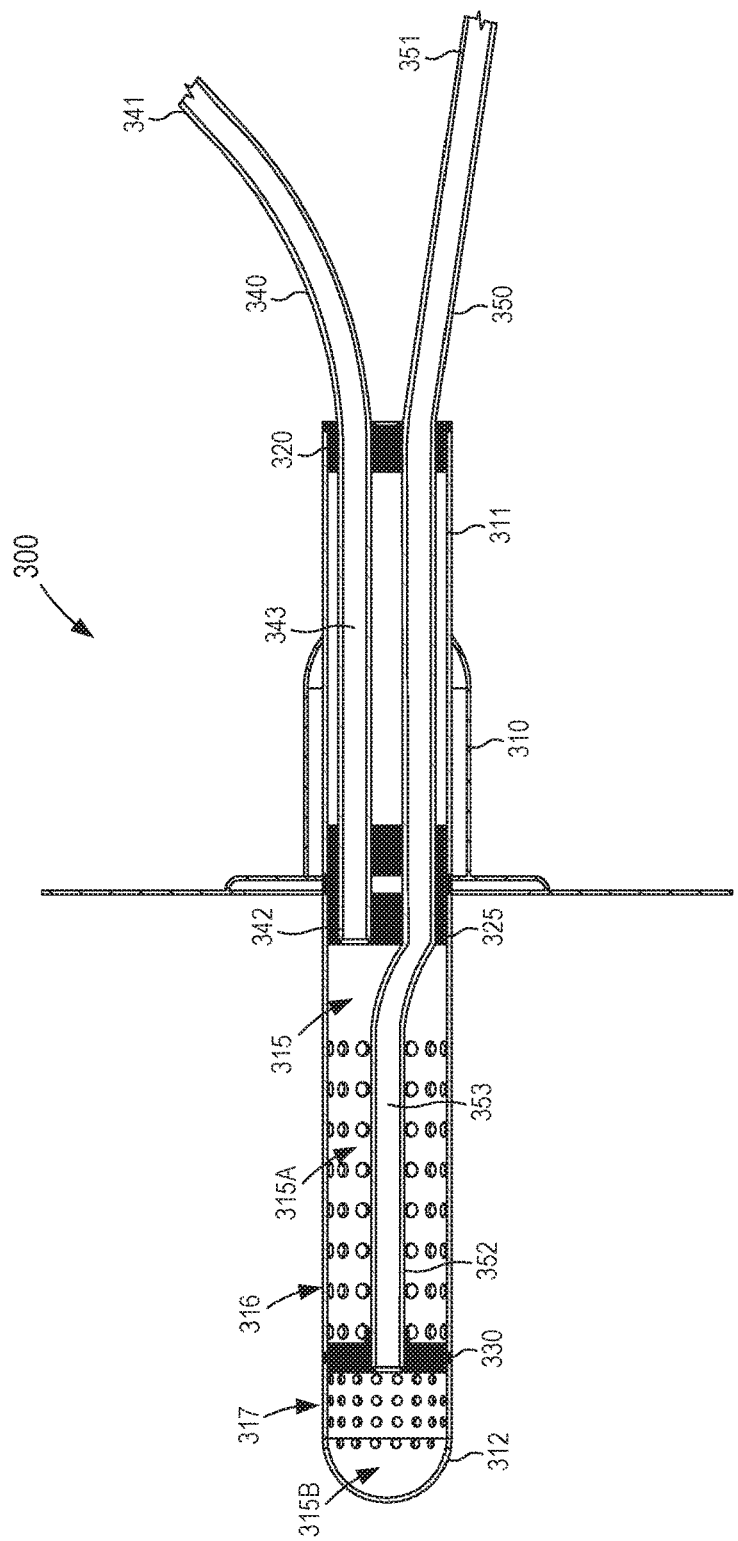
FIG. 11 is a cross-sectional side view of a body cavity cleansing device according to another embodiment.

While the housing 210, the first cannula device 240, and the second cannula 250 are particularly shown and described above with reference to FIGS. 3-10, in other embodiments, a device can include a housing, a first cannula, and a second cannula in any suitable arrangement or configuration. For example, FIG. 11 illustrates a body cavity cleansing device 300 according to another embodiment. The body cavity cleansing device 300 (also referred to herein as "device") includes a housing 310, a first cannula 340, and a second cannula 350. The housing 310 includes a proximal end portion 311 and a distal end portion 312, and defines an inner volume 315. The housing 310 can be any suitable shape, size, or configuration. For example, in some embodiments, the housing 310 can be substantially similar to the housing 210 described above with reference to FIGS. 3-10. In this manner, the housing 310 is briefly described herein to introduce salient features but similar aspects are not described in further detail herein.

The proximal end portion 311 of the housing 310 is substantially open and is configured to receive a portion of the first cannula 340 and the second cannula 350. The proximal end portion 311 of the housing 310 is coupled to a proximal seal member 320 configured to form a substantially fluid tight seal with the proximal end portion 311 of the housing 310, as described in detail above with reference to the distal seal member 220 and the housing 210. The distal end portion 312 of the housing 310 is closed. That is to say, the distal end portion 312 includes a continuous distal surface (e.g., does not define a distal opening) or the like. In some embodiments, the distal surface can, for example, facilitate the breaking apart and/or releasing of undesired matter from, for example, an inner surface of an anatomical structure defining a cavity or lumen, as described above.

As shown in FIG. 11, the housing 310 defines a first set of openings 316 and a second set of openings 317. The first set of openings 316 are arranged along a first portion of the housing 310, wherein each opening extends through a wall of the housing 310 to be in fluid communication with, for example, a first portion 315A of the inner volume 315. Similarly, the distal end portion 312 can define the second set of openings 317 arranged along a second portion of the housing 310, wherein each opening extends through the wall of the housing 310 to be in fluid communication with, for example, a second portion 315B of the inner volume 315. The first set of openings 316 and the second set of openings 317 can be any suitable arrangement and each opening can have any suitable size. For example, first set of openings 316 and the second set of openings 317 can be substantially similar to the first set of openings 216 and the second set of openings 217 defined by the housing 210.

The arrangement of the housing 310 is such that the first portion 315A of the inner volume 315 is substantially fluidically isolated from the second portion 315B of the inner volume 315. For example, as shown in FIG. 11, the housing 310 includes and/or otherwise houses a proximal seal member 320, a medial seal member 325, and a distal seal member 330. The proximal seal member 320 can be any suitable seal or elastomeric member configured to be placed in contact with an inner surface of the housing 310 to define a substantially fluid tight seal therebetween. For example, the proximal seal member 320 can be substantially similar to the proximal seal member 220 included in the housing 210. As such, the proximal seal member 320 is configured to receive a portion of the first cannula 340 and the second cannula 350, as described in detail above.

The medial seal member 325 is disposed within the inner volume 315 in a medial position along the housing 310. As shown in FIG. 11, the medial seal member 325 receives and/or couples to a distal end portion 342 of the first cannula 340 and receives a portion of the second cannula 350. Expanding further, a distal end portion 352 of the second cannula 350 extends through the medial seal member 325 to be disposed in a distal position relative thereto, as described in further detail herein.

The distal seal member 330 is disposed within the inner volume 315 in a distal position along the housing 310. As shown in FIG. 11, the distal seal member 330 receives and/or is coupled to the distal end portion 352 of the second cannula 350. The arrangement of the medial seal member 325, the distal seal member 330, and the second cannula 350, for example, collectively define, separate, and/or isolate the inner volume 315 of the housing 310 into the first portion 315A and the second portion 315B. More specifically, the portion of the inner volume 315 disposed between the medial seal member 325 and the distal seal member 330 defines the first portion 315A of the inner volume 315, while the portion of the inner volume 315 that is distal to the distal seal member 330 defines the second portion 315B of the inner volume 315, as described above with reference to the housing 210. Thus, the arrangement of the medial seal member 325, the distal seal member 330, and the second cannula 350 is such that the first portion 315A of the inner volume 315 is substantially fluidically isolated from the second portion 315B of the inner volume 315 and as such, the second cannula 350 is in fluid communication with the second portion 315B of the inner volume 315, while being fluidically isolated from the first portion 315A of the inner volume 315, as described in further detail herein.

The first cannula 340 of the device 300 has a proximal end portion 341 and the distal end portion 342 and defines a lumen 343 therethrough. The proximal end portion 341 of the first cannula 340 can be operably coupled to a vacuum source (not shown in FIG. 11) such that the lumen 343 is placed in fluid communication therewith, as described in detail above with reference to the first cannula 240. Although not shown in FIG. 11, in some embodiments, the proximal end portion 341 is inserted through and/or otherwise partially disposed in, a flow control mechanism such as, for example, the flow control mechanism 245 described above with reference to FIG. 6. Thus, such a flow control mechanism can be transitioned from a first configuration to a second configuration to substantially obstruct and/or pinch the lumen 343, thereby fluidically isolating the proximal end portion 341 of the first cannula 340 from the distal end portion 342. The distal end portion 342 of the first cannula 340 is disposed within the housing 310. More specifically, the distal end portion 342 of the first cannula 340 can be inserted through the proximal seal member 320 and coupled to and/or inserted through the medial seal member 325. In this manner, the lumen 343 of the first cannula 340 is in fluid communication with the first portion 315A of the inner volume 315, as shown in FIG. 11. As such, the first portion 315A of the inner volume 315 and the lumen 343 of the first cannula 340 define a fluid flow path between the first set of openings 316 and the vacuum source (not shown), as described in further detail herein.

The second cannula 350 of the device 300 has a proximal end portion 351 and the distal end portion 352 and defines a lumen 353 therethrough. The proximal end portion 351 of the second cannula 350 can be operably coupled to a fluid reservoir (not shown in FIG. 11) such that the lumen 353 is placed in fluid communication therewith, as described in detail above with reference to the second cannula 250. Although not shown in FIG. 11, in some embodiments, the proximal end portion 351 of the second cannula 350 is inserted through and/or otherwise partially disposed in, a flow control mechanism such as, for example, the flow control mechanism 255 described above with reference to FIG. 6. Thus, such a flow control mechanism can be transitioned from a first configuration to a second configuration to substantially obstruct and/or pinch the lumen 353 of the second cannula 350, thereby fluidically isolating the proximal end portion 351 from the distal end portion 352.

The distal end portion 352 of the second cannula 350 is disposed within the housing 310. More specifically, the distal end portion 352 of the second cannula 350 can be inserted through the proximal seal member 320 and the medial seal member 325, and coupled to and/or inserted through the distal seal member 330. In other words, while the device 200 described above includes the conduit 335 that defined a fluid flow path between the medial seal member 325 and the distal seal member 330, in this embodiment, the distal end portion 352 of the second cannula 350 extends through the medial seal member 325, the first portion 315A of the inner volume 315, and the distal seal member 330 to place the lumen 353 in fluid communication with the second portion 315B of the inner volume 315, as shown in FIG. 11. Thus, as described above, the lumen 353 of the second cannula 350 is in fluid communication with the second portion 315B of the inner volume 315 while being fluidically isolated from the first portion 315A of the inner volume 315. As such, the second portion 315B of the inner volume 315 and the lumen 353 of the second cannula 350 define a fluid flow path between the second set of openings 317 and the fluid source (not shown), as described in further detail herein. In this manner, the device 300 can be used, for example, to cleanse contaminants from a cavity and/or lumen defined, for example, by the lower GI tract 10 in a substantially similar manner as described in detail above with reference to the device 200.

Figure 12:
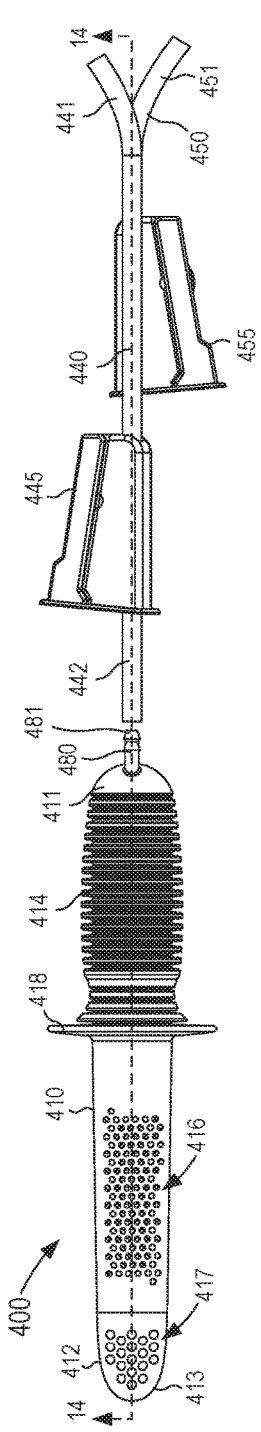
FIG. 12 is a top view of a body cavity cleansing device according to another embodiment.
Figure 13:
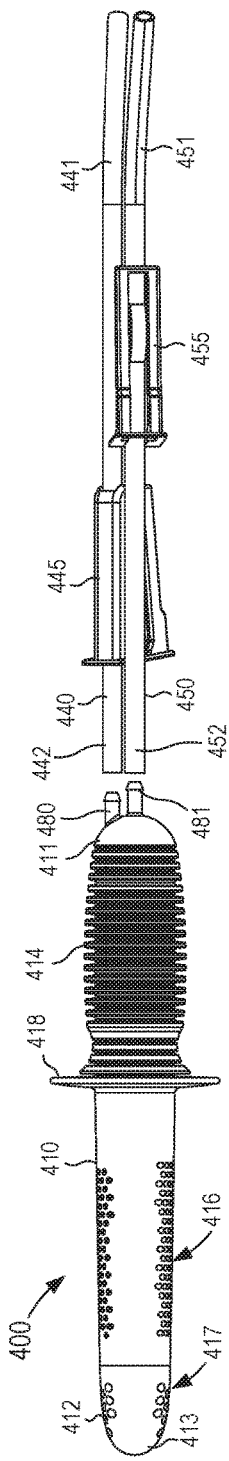
FIG. 13 is a side view of the body cavity cleansing device of FIG. 12.
Figure 14:
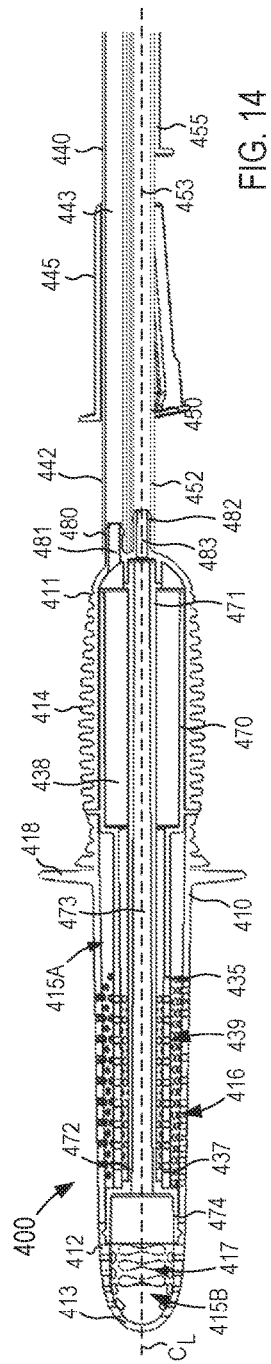
FIG. 14 is a cross-sectional side view of the body cavity cleansing device of FIG. 12, taken along the line 14-14 in FIG. 12.

FIGS. 12-14 illustrate a body cavity cleansing device 400 according to another embodiment. The body cavity cleansing device 400 (also referred to herein as "device") includes a housing 410, a first cannula 440, and a second cannula 450. In some instances, the device 400 is used to facilitate the cleaning of a body cavity such as, for example, a portion of the lower GI tract 10 illustrated in FIG. 1. Specifically, a portion of the housing 410 can be inserted through the anus 18 to gain access to a cavity (e.g., a lumen or the like) defined by the rectum 17 and/or the colon 14, thereby allowing the device 400 to be used to clean substantially all of the lower GI tract 10, as described in detail above with reference to FIGS. 3-10.

As shown in FIGS. 12-14, the housing 410 has a proximal end portion 411 and a distal end portion 412 and defines an inner volume 415 (FIG. 14). The housing 410 can be any suitable shape, size, or configuration. For example, the arrangement of the housing 410 can substantially correspond to an anatomical structure of the lower GI tract 10. By way of example, the size, shape, and stiffness of the housing 410 can be suitable for insertion into the body (i.e., via the anus 18), while limiting discomfort and/or substantially preventing injury of the patient. Furthermore, as shown in FIGS. 12 and 13, the housing 410 includes and/or is coupled to a flange 418 (e.g., a guard, shield, barrier, and/or the like) configured to limit an amount of fluid undesirably flowing outside of the body and/or device 400.

The proximal end portion 411 of the housing 410 includes and/or forms a handle 414, a first port 480, and a second port 481. The handle 414 can be any suitable shape, size, or configuration. In some embodiments, the handle 414 can be formed by any suitable number of flanges and/or plates, which collectively define a contour of the handle 414. In this manner, the handle 414 can form an ergonomic shape and/or configuration that can facilitate, for example, single-handed use of the device 400. The first port 480 extends from the handle 414 and defines a lumen 481. As described in further detail herein, the first port 480 is in fluid communication with a first conduit 435 disposed within the housing 410 and is configured to be physically and fluidically coupled to the first cannula 440 (FIG. 14). Similarly, the second port 482 is in fluid communication with a second conduit 470 disposed within the housing 410 and is configured to be physically and fluidically coupled to the second cannula 450 (FIG. 14).

The distal end portion 412 of the housing 410 is closed. That is to say, the distal end portion 412 includes a continuous distal surface 413 (e.g., does not define an opening through a distal most surface) or the like. In the embodiment shown in FIGS. 12-14, the distal surface 413 has a substantially bullet-shape and/or is otherwise rounded or curved. In some embodiments, the rounded distal surface 413 can, for example, limit and/or otherwise substantially prevent the housing 410 from damaging tissue or the like while being placed into a desired position within the body. Moreover, the walls of the distal end portion 412 of the housing 410 can have any suitable thickness and/or can be formed from any suitable material that can allow, for example, the distal end portion 412 to elastically deform in response to an applied force such as when navigating the housing 410 within a tortuous path within the body, which in turn, can substantially reduce and/or prevent damage to surrounding tissue. Although the distal surface 413 is particularly shown in FIG. 14 as being hollow, in other embodiments, the distal end portion 412 can include, for example, a distal tip or the like that is substantially solid, as described above with reference to the housing 210.

As shown, the housing 410 defines a first set of openings 416 and a second set of openings 417. The sets of openings 416 and 417 can be any suitable shape, size, and/or configuration. For example, in some embodiments, the arrangement and/or configuration of the sets of openings 416 and 417 can be substantially similar to the set of openings 216 and 217, respectively, described above with reference to FIGS. 3-10. Therefore, some aspects of the sets of openings 416 and 417 are not described in further detail herein. As shown in FIG. 14, the first set of openings 416 are included in and/or form a pattern of openings at or near a first, proximal region along a longitudinal centerline $C_L$ of the housing 410, and the second set of openings 417 are included in and/or form a pattern of openings at or near a second, distal region along the longitudinal centerline $C_L$ of the housing 410. In this manner, the first set of openings 416 are in fluid communication with a first portion 415A of the inner volume 415, while the second set of openings 417 are in fluid communication with a second portion 415B of the inner volume 415, distal to the first portion 415A.

The arrangement of the housing 410 is such that the first portion 415A of the inner volume 415 is substantially fluidically isolated from the second portion 415B of the inner volume 415. For example, as shown in FIGS. 6-9, the housing 410 includes and/or otherwise houses a proximal seal member 420, a medial seal member 425, and a distal seal member 430. The proximal seal member 420 can be any suitable seal or elastomeric member configured to contact an inner surface of the housing 410 to define a substantially fluid tight seal therebetween. For example, in some embodiments, at least a portion of the proximal seal member 420 can have an outer diameter that is greater than an inner diameter of the housing 410. Thus, when disposed within the inner volume 415, the proximal seal member 420 forms a friction fit with the inner surface of the housing 410, which is sufficient to form a substantially fluid tight seal therebetween. Moreover, the proximal seal member 420 defines a first opening 421 and a second opening 422 configured to receive a portion of the first cannula 440 and the second cannula 450, respectively, as described in further detail herein (see e.g., FIG. 7). Although not shown in FIG. 7, in some embodiments, the proximal seal member 420 is configured to be in contact with a portion the first cannula 440 and a portion of the second cannula 450 disposed in the openings 421 and 422, respectively, to form and/or define a fluid tight seal. Thus, the proximal seal member 420 substantially fluidically seals the proximal end portion 411 of the housing 410, as described in further detail herein.

As described above, the housing 410 includes, encloses, and/or otherwise houses the first conduit 435 and the second conduit 470. The first conduit 435 has a proximal end portion 436 and a distal end portion 437 and defines a lumen 438 extending therethrough. The proximal end portion 436 of the first conduit 435 is at least fluidically coupled to the first port 480 such that the lumen 438 of the first conduit 435 and the lumen 481 of the first port 480 are in fluid communication. The distal end portion 437 of the first conduit 435 extends through a portion of the inner volume 415 of the housing 410 and is in contact with and/or otherwise adjacent to a distal end portion 472 of the second conduit 470, as described in further detail herein. The distal end portion 437 of the first conduit 435 defines a set of openings 439 that extend through the walls of the first conduit 435. As such, the openings 439 place the lumen 438 of the first conduit 435 in fluid communication with a volume outside of the first conduit 410. In other words, the set of openings 439 places the lumen 438 of the first conduit 435 in fluid communication with a portion of the inner volume 415 of the housing 410 (e.g., the first portion 415A of the inner volume 415).

The second conduit 470 has a proximal end portion 471 and a distal end portion 472 and defines a lumen 473 extending therethrough. As shown in FIG. 14, at least a portion of the second conduit 470 is disposed within the lumen 438 defined by the first conduit 435. The proximal end portion 471 of the second conduit 470 is at least fluidically coupled to the second port 482 such that the lumen 473 of the second conduit 470 and the lumen 483 of the second port 482 are in fluid communication. The distal end portion 472 of the second conduit 470 extends through a portion of the inner volume 415 of the housing 410 and is in contact with and/or otherwise adjacent to a distal end portion 437 of the first conduit 435. More specifically, the distal end portion 472 of the second conduit 470 includes a flange 474 or flared region. In this embodiment, the flange 474 has a diameter that is greater than a diameter of the remaining portions of the second conduit 470. In addition, the diameter of the flange 474 is associated with an inner diameter of the housing 410. In some embodiments, this arrangement is such that an outer surface of the flange 474 and an inner surface of the housing 410 are in physical contact to collectively define a substantially fluid tight seal. As shown in FIG. 14, the distal end portion 472 of the second conduit 470 is open and, as such, the lumen 473 of the second conduit 470 is in fluid communication with the second portion 415B of the inner volume 415 and the second set of openings 417 defined by the housing 410.

As described above, a portion of the second conduit 470 is disposed within the lumen 438 defined by the first conduit 435. In this manner, at least a portion of the second conduit 470 has a diameter that is sufficiently small and/or at least a portion of the first conduit 435 defines an inner diameter that is sufficiently large to allow at least the portion of the second conduit 470 to be disposed within the lumen 438 of the first conduit 435. As shown in FIG. 14, the distal end portion 437 of the first conduit 435 abuts a proximal surface of the flange 474 of the second conduit 470. In other words, the flange 474 is disposed in a distal position relative to the first conduit 435 and thus, is not disposed within the lumen 438 defined by the first conduit 435. Moreover, the arrangement of the distal end portion 437 of the first conduit 435 is such that the distal end portion 437 of the first conduit 435 and the proximal surface of the flange 474 against which it abuts, collectively define a fluid tight seal.

With the flange 474 being disposed distal to the first conduit 435 and forming a fluid tight seal with the inner surface of the housing 410 and with the flange 474 and the distal end portion 437 of the first conduit 435 collectively forming a fluid tight seal, the lumen of the first conduit 438 is fluidically isolated from the lumen 473 of the second conduit 470. In addition, this arrangement is such that the first portion 415A of the inner volume 415 of the housing 410 is fluidically isolated from the second portion 415B of the inner volume 415 of the housing 410. In other words, the portion of the inner volume 415 disposed between the flange 474 and a distal inner surface (through which the lumen 481 of the first port 480 extends) defines the first portion 415A of the inner volume 415 and the portion of the inner volume 415 that is distal to the flange 474 defines the second portion 415B of the inner volume 415.

When referring to the substantially fluidic isolation between the first portion 415A of the inner volume 415 and the second portion 415B of the inner volume 415, the fluidic isolation therebetween is described relative to the inner volume 415 defined by the housing 410. Thus, while the first set of openings 416 and the second set of openings 417 place the first portion and the second portion, respectively, of the inner volume 415 in fluid communication with a volume substantially outside of the housing 410, which in turn, may place the first set of openings 416 and the second set of openings 417 in fluid communication, the first portion 415A of the inner volume 415 and the second portion 415B of the inner volume 415 are nonetheless substantially fluidically isolated within the context of the inner volume 415 defined by the housing 410.

The first cannula 440 of the device 400 has a proximal end portion 441 and the distal end portion 442 and defines a lumen 443 therethrough. As shown, portion of the first cannula 440 is inserted through and/or otherwise partially disposed in a flow control mechanism 445. The flow control mechanism 445 can be any suitable device, mechanism, member, assembly, and/or the like configured to selectively control a flow of the through the lumen 443 defined by the first cannula 440. For example, in some embodiments, the flow control mechanism 445 can be substantially similar to the flow control mechanism 245 described above with reference to the device 200 in FIGS. 3-10. Thus, the flow control mechanism 445 is not described in further detail herein.

The proximal end portion 441 of the first cannula 440 can be operably coupled to a vacuum source (not shown in FIGS. 12-14), which in turn, places the lumen 443 in fluid communication with the vacuum source. For example, in some embodiments, the proximal end portion 441 can be physically and fluidically coupled to an inlet of a vacuum source or pump. The vacuum source can be any suitable device such as a pump configured to produce a negative pressure differential between a portion of the pump and the inlet of the vacuum source. Thus, when the first cannula 440 is fluidically coupled to the inlet (e.g., either directly or indirectly), activation of the vacuum source results in a suction force within the lumen 443 of the first cannula 440, as described in further detail herein.

The distal end portion 442 of the first cannula 440 is physically and fluidically coupled to the first port 480. For example, in some embodiments, at least a portion of the first port 480 can be inserted into the lumen 443 defined by the first cannula 440. As such, the lumen 481 of the first port 480 is in fluid communication with the lumen 443 of the first cannula 440, which in turn, places the lumen 443 of the first cannula 440 in fluid communication with the lumen 438 of the first conduit 435. Moreover, the lumen 438 of the first conduit 435 is placed in fluid communication with the first portion 415A of the inner volume 415 via the set of openings 439 and the first portion 415A of the inner volume 415 is, in turn, in fluid communication with a volume outside of the housing 410 via the first set of openings 416. Thus, the lumen 443 of the first cannula 440, the lumen 481 of the first port 480, the lumen 438 of the first conduit 435, the set of openings 439 defined by the first conduit 435, and the first set of openings 416 defined by the housing 410 collectively define a fluid flow path that can place a vacuum source in fluid communication with a volume outside of the housing 410.

The second cannula 450 of the device 400 has a proximal end portion 451 and the distal end portion 452 and defines a lumen 453 therethrough. As described above with reference to the first cannula 440, a portion of the second cannula 450 is inserted through and/or otherwise partially disposed in a flow control mechanism 455. The flow control mechanism 455 can be any suitable device, mechanism, member, assembly, and/or the like configured to selectively control a flow of the through the lumen 453 defined by the second cannula 450.

The proximal end portion 451 of the second cannula 450 can be operably coupled to a fluid reservoir (not shown in FIGS. 12-14), which in turn, places the lumen 453 in fluid communication with the fluid reservoir. For example, in some embodiments, the proximal end portion 451 can be physically and fluidically coupled to an outlet of a fluid reservoir or the like containing sterile water or saline. In other embodiments, the proximal end portion 451 of the second cannula 450 can be coupled to the fluid source via an intervening structure such as, for example, a locking mechanism, a valve, a coupler, flexible sterile tubing, and/or the like.

The distal end portion 452 of the second cannula 450 is physically and fluidically coupled to the second port 482. For example, in some embodiments, at least a portion of the second port 482 can be inserted into the lumen 453 defined by the second cannula 450. As such, the lumen 483 of the second port 482 is in fluid communication with the lumen 453 of the second cannula 450, which in turn, places the lumen 453 of the second cannula 450 in fluid communication with the lumen 473 of the second conduit 470. Moreover, the lumen 473 of the second conduit 470 is in fluid communication with the second portion 415B of the inner volume 415 (e.g., via the open distal end portion 472 and/or flange 474) and the second portion 415B of the inner volume 415 is, in turn, in fluid communication with a volume outside of the housing 410 via the second set of openings 417. Thus, the lumen 453 of the second cannula 450, the lumen 483 of the second port 482, the lumen 473 of the second conduit 470, and the second set of openings 417 defined by the housing 410 collectively define a fluid flow path that can place a fluid reservoir and/or source in fluid communication with a volume outside of the housing 410.

In use, a user can manipulate the device 400, for example, by fluidically coupling the first cannula 440 to the vacuum source and the second cannula 450 to the fluid source. The user can then manipulate the device 400 by inserting at least a portion of the housing 410 into, for example, the anus 18 of the body (e.g., his or her body or in the case of a user being a medical professional, a patient's body) such that the first set of openings 416 and the second set of openings 417 are disposed within a portion of the anal canal, the rectum 417, or the colon 14 of the lower GI tract (see e.g., FIG. 1). In some instances, the housing 410 can be inserted in to the patient's body at a desired depth that can, for example, place the flange 418 in contact with the skin of the patient.

With the housing 410 disposed in the desired position within, for example, the lower GI tract 10, the user can actuate the device 400 and/or the vacuum source and the fluid source (not shown in FIGS. 12-14). Specifically, the fluid source, once actuated, can produce a pressurized flow of sterile water or saline ("fluid"), which in turn, flows through the lumens 453, 483, and 473 of the second cannula 450, second port 482, and second conduit 470, respectively, and into the second portion 415B of the of the inner volume 415. In some instances, the flow rate of the fluid (e.g., as produced by a pump or the like included in the fluid source) is such that, a volume of the fluid fills the second portion 415B of the inner volume 415 and thus, once the second portion 415B of the inner volume 415 is substantially filled, an additional flow of fluid increases the pressure within the second portion 415B of the inner volume 415, which forces a pressurized flow of the fluid through the second set of openings 417 and into the body cavity.

In a substantially concurrent process, the vacuum source can be actuated to produce a negative pressure differential between the vacuum source and the lumen 443 of the first cannula 440 (as described above). In this manner, the negative pressure differential produces a suction force within the lumens 443, 481, and 438 of the first cannula 440, first port 480, and first conduit 435, respectively. The suction force or negative pressure within the lumen 438 of the first conduit 435 produces a suction force and/or negative pressure within the first portion 415A of the inner volume 415 of the housing 410 via the openings 439 defined by the first conduit. The suction force and/or negative pressure within the first portion 415A of the inner volume 415, in turn, draws a volume of fluid into the first portion 415A of the inner volume 415 via the first set of openings 416.

As such, the device 400 can provide lavage of the lower GI tract 10. More specifically, the pressurized flow of sterile water or saline flows through the second cannula 450 and the second set of openings 417 and into the lumen or cavity defined by a portion of the lower GI tract 10, which in turn, can rinse, cleanse, break apart, and/or otherwise solubilize undesired matter (e.g., fecal matter, pus, blood, undigested food particles, bacteria, etc.). In addition, the distal surface 413 of the housing 410 can engage such undesired matter, thereby aiding the pressurized flow of fluid in breaking apart the matter. The suction force exerted through the first set of openings 416 draws such undesired matter that is broken apart, solubilized, and/or otherwise released by the pressurized flow of sterile water or saline, as well as a waste portion of the used fluid (i.e., no longer sterile) into the first portion 415A of the inner volume 415. Thus, the undesired matter is drawn through the first set of openings 416 defined by the housing 410 and into the first portion 415A of the inner volume 415; through the set of openings 439 defined by the first conduit 435 and into the lumen 438 of the first conduit 435; and through the lumens 481 and 443 of the first port 480 and first cannula 440, respectively, into, for example, a waste reservoir or storage fluidically coupled to the vacuum source. In this manner, the device 400 can be used, for example, to cleanse contaminants from a cavity and/or lumen defined, for example, by the lower GI tract 10.

Figure 15:
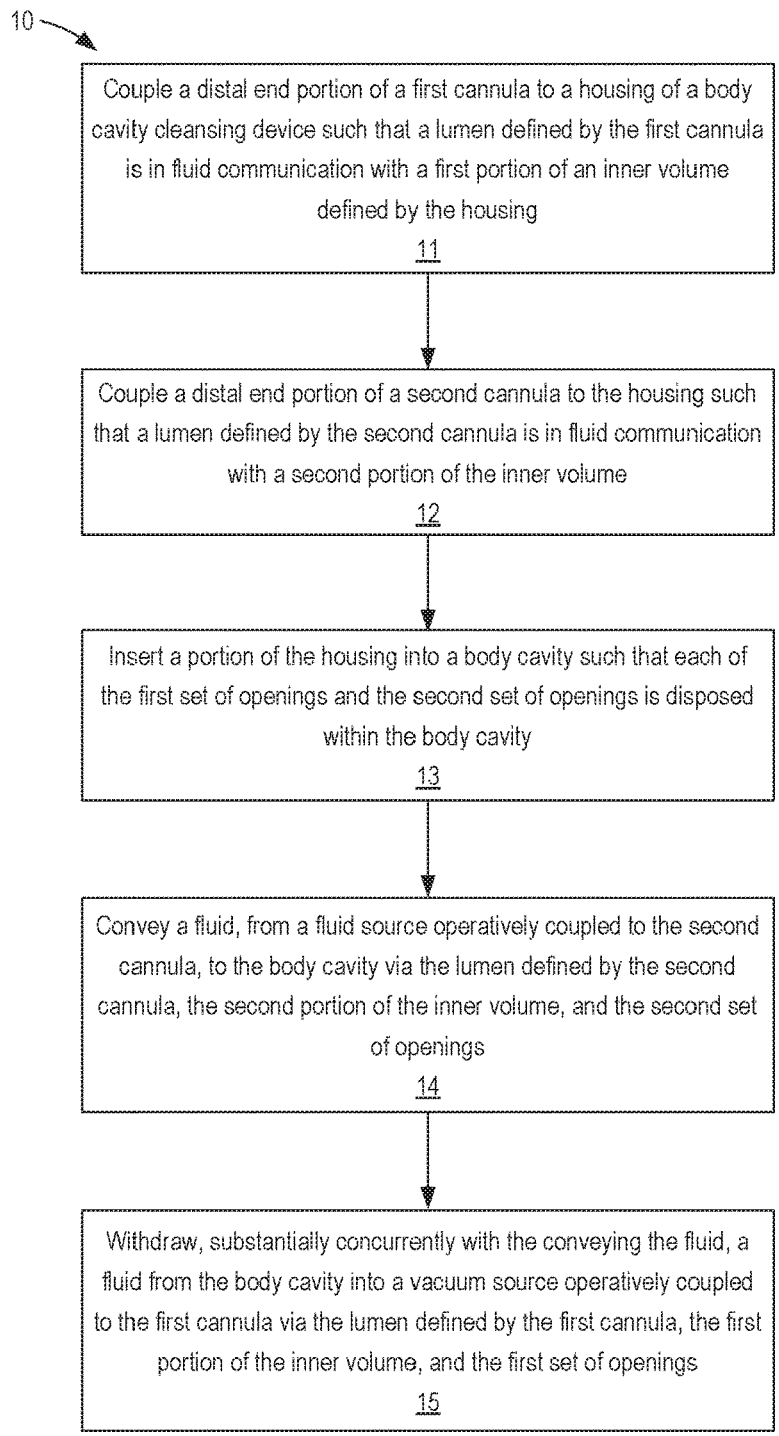
FIG. 15 is a flowchart illustrating a method of using a body cavity cleansing device according to an embodiment.

Referring now to FIG. 15, a flowchart illustrates a method 10 of using a body cavity cleansing device according to an embodiment. The body cavity cleansing device can be any suitable cleansing device configured to cleanse a body cavity such as, for example, at least a portion of the lower GI track, as described in detail above. For example, in some embodiments, the body cavity cleansing device (also referred to herein as "device") includes a housing that defines an inner volume, a first set of openings in fluid communication with a first portion of the inner volume, and a second set of openings in fluid communication with a second portion of the inner volume. The first portion of the inner volume is fluidically isolated from the second portion of the inner volume. In some embodiments, the device can be, for example, any of the devices 100, 200, 300, and/or 400 described herein.

The method 10 includes coupling a distal end portion of a first cannula to the housing such that a lumen defined by the first cannula is in fluid communication with the first portion of the inner volume, at 11. For example, in some embodiments, the housing can include a first port or the like configured to be coupled to the distal end portion of the first cannula. In some embodiments, the device can also include a conduit or the like (e.g., a first conduit) disposed within the inner volume and configured to place the first port in fluid communication with, for example, the first portion of the inner volume. For example, in some embodiments, the device can include a conduit similar to the first conduit 435 included in the device 400, described above with reference to FIGS. 12-14. Moreover, a proximal end portion of the first cannula can be operatively coupled to a vacuum source or the like. In some instances, the proximal end portion of the first cannula can be, for example, preassembled with the vacuum source. In other embodiments, the method 10 can include operatively coupling the proximal end portion of the first cannula to the vacuum source.

A distal end portion of a second cannula is coupled to the housing such that a lumen defined by the second cannula is in fluid communication with the second portion of the inner volume, at 12. For example, the housing can include a second port or the like configured to be coupled to the distal end portion of the second cannula. As described above, in some embodiments, the device can include a second conduit (e.g., the second conduit 470 included in the device 400) disposed within the inner volume and configured to place the second port in fluid communication with, for example, the second portion of the inner volume. In some embodiments, a portion of the second conduit can be disposed within a lumen defined by the first conduit, as described in detail above with reference to the device 400. Moreover, as described above with reference to the first cannula, a proximal end portion of the second cannula can be operatively coupled to a fluid source or reservoir. In some instances, the method 10 can include operatively coupling the proximal end portion of the second cannula to the fluid source.

A portion of the housing is inserted into the body cavity such that each of the first set of openings and the second set of openings is disposed within the body cavity, at 13. In some embodiments, the device and/or the housing can include a flange or the like configured to limit and/or define a depth at which the housing can be inserted into the body cavity. In some embodiments, the flange can be moved along a length of the housing to adjust the insertion depth of the housing, as described above with reference to the device 200.

With the desired portion of the housing disposed in the body cavity, a fluid is conveyed from the fluid source to the body cavity via the lumen defined by the second cannula, the second portion of the inner volume, and the second set of openings, at 14. In a substantially concurrent process, a fluid is withdrawn from the body cavity into the vacuum source via the lumen defined by the first cannula, the first portion of the inner volume, and the first set of openings, at 15. In this manner, the device can be used to deliver a fluid into a body cavity and to remove (e.g., via suction) a waste fluid and/or contaminants in a substantially concurrent process to cleanse the body cavity, as described in detail above with reference to the devices 100, 200, 300, and/or 400.

The components of body cavity cleansing devices described herein (i.e., the devices 100, 200, 300, and/or 400) can be packaged together or separately. For example, the housing 210 can be coupled to and/or assembled with the first cannula 240 and the second cannula 250 and packaged together. In other embodiments, the housing 210 can be packaged independent of the first cannula 240 and the second cannula 250. In such embodiments, a user can couple the first cannula 240 and the second cannula 250 to the housing 210 (in the manner described above) prior to use. In this manner, certain components of the devices 200 and/or 300 can be disposable (e.g., the first cannulas 240 and 340 and the second cannulas 250 and 350), while other components are reusable (e.g., the housings 210 and 310), after being sterilized. Each of the components discussed herein can be unitarily constructed or can be a combination of parts.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. For example, while the cannulas 240 and 250 of the device 200 are described above with reference to FIGS. 3-10 as extending through the proximal seal member 220 to couple to the coupling portions 226 and 228, respectively, of the medial seal member 225, in other embodiments, a device can include a set of conduits extending between a proximal seal member and a distal seal member. For example, in some embodiments, a device can include a first conduit configured to define a fluid flow path between a first portion or opening of a proximal seal member and a first portion or opening of a medial seal member, and a second conduit configured to define a fluid flow path between a second portion or opening of the proximal seal member and a second portion or opening of the medial seal member. Thus, in such embodiments, a first cannula can be coupled to the first portion of the proximal seal member to be placed in fluid communication with the first conduit and a second cannula can be coupled to the second portion of the proximal seal member to be placed in fluid communication with the second conduit. Moreover, in some such embodiments, the second conduit can extend through the medial seal member to be coupled to, for example, a distal seal member, as described above with reference to the conduit 235 of the device 200.

Although various embodiments have been described as having particular features and/or combinations of components, other embodiments are possible having a combination of any features and/or components from any of embodiments as discussed above. The specific configurations of the various components can also be varied. For example, the size and specific shape of the various components can be different from the embodiments shown, while still providing the functions as described herein. By way of example, the size and shape of the various components can be specifically selected for a desired rate of fluid flow. More specifically, while the first set of openings 216 and 316 and the second set of openings 217 and 317 are particularly shown and described above, in other embodiments, the size, diameter, shape, arrangement and/or the like of the openings can be modified to, for example, increase a pressure within the a fluid of fluid exiting the second set of openings 217 and 317. In some embodiments, the size, diameter, shape, arrangement and/or the like of the openings included in the first set of openings 216 and 316 can similarly be varied to, for example, increase or decrease a suction force therethrough.

Any components of the devices 100, 200, 300, and 400 can be formed from any suitable biocompatible material such as those described above. In some embodiments, various components of the devices 100, 200, 300, and 400 can be formed from a biocompatible material selected because of physical and/or mechanical properties thereof. For example, in some embodiments, the first cannulas 140, 240, 340, and 440 can be formed from a biocompatible material that is relatively flexible to allow for bending and/or flexing in use or storage, while having a sufficient durometer, rigidity, and/or hardness to substantially prevent and/or limit deformation of the first cannulas 140, 240, 340, and 440 in response to being exposed to the suction force produced by a vacuum source.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed:

1. An apparatus, comprising:
a housing have a proximal end portion and a distal end portion and defining an inner volume, the proximal end portion of the housing including a first port and a second port, the housing defining a first plurality of openings in fluid communication with a first portion of the inner volume and a second plurality of openings in fluid communication with a second portion of the inner volume, the first portion of the inner volume being fluidically isolated from the second portion of the inner volume;
a first conduit disposed in the inner volume, the first conduit having a proximal end portion and a distal end portion and defining a lumen therethrough, the distal end portion of the first conduit defining a plurality of openings that places the lumen of the first conduit in fluid communication with the first portion of the inner volume, the lumen of the first conduit being in fluid communication with a lumen defined by the first port;
a second conduit having a proximal end portion and a distal end portion and defining a lumen therethrough, the second conduit being at least partially disposed within the lumen of the first conduit, the lumen of the second conduit defining a fluid flow path between the second portion of the inner volume and a lumen defined by the second port, the lumen of the second conduit being fluidically isolated from the lumen of the first conduit;
a first cannula having a proximal end portion and a distal end portion and defining a lumen therethrough, the proximal end portion of the first cannula configured to be placed in fluid communication with a vacuum source, the distal end portion of the first cannula configured to be coupled to the first port to place the lumen of the first cannula in fluid communication with the lumen of the first conduit; and
a second cannula having a proximal end portion and a distal end portion and defining a lumen therethrough, the proximal end portion of the second cannula configured to be placed in fluid communication with a fluid source, the distal end portion of the second cannula configured to be coupled to the second port to place the lumen of the second cannula in fluid communication with the lumen of the second conduit.

2. The apparatus of claim 1, wherein the vacuum source is configured to produce a negative pressure within the first portion of the inner volume operative to draw fluid through the first set of openings and into the first portion of the inner volume,
the fluid source is configured to deliver a flow of fluid to the second portion of the inner volume, a positive pressure within the second portion of the inner volume operative to produce a flow of fluid from the second portion of the inner volume through the second set of openings.

3. The apparatus of claim 1, wherein each opening from the first plurality of openings has a first size, each opening from the second plurality of openings has a second size, the second size being different from the first size.

4. The apparatus of claim 1, wherein the first plurality of openings includes a first number of openings, the second plurality of openings includes a second number of openings, the first number of openings being different from the second number of openings.

5. The apparatus of claim 1, further comprising:
a first flow control mechanism, the first flow control mechanism is disposed about a portion of the first cannula and is configured to control a flow of fluid through the lumen of the first cannula; and
a second flow control mechanism, the second flow control mechanism is disposed about a portion of the second cannula and is configured to control a flow of fluid through the lumen of the second cannula.

6. The apparatus of claim 1, wherein the distal end portion of the second conduit includes a flange, the flange being disposed in a distal position relative to the first conduit, an outer surface of the flange is in contact with an inner surface of the housing to collectively define a substantially fluid tight seal therebetween operative to fluidically isolate the first portion of the inner volume from the second portion of the inner volume.

7. The apparatus of claim 6, wherein the proximal end portion of the first conduit is in contact with an inner surface of the housing to collectively define a substantially fluid tight seal therebetween, the first portion of the inner volume is defined between flange of the second conduit and the proximal end portion of the first conduit.

* * * * *